United States Patent
Samant et al.

(10) Patent No.: US 11,376,277 B2
(45) Date of Patent: Jul. 5, 2022

(54) SYNERGISTIC MEDICINAL COMPOSITIONS FOR TREATING DYSFUNCTIONAL D-SERINE SIGNALING

(71) Applicant: CELAGENEX RESEARCH (INDIA) PVT. LTD., Maharashtra (IN)

(72) Inventors: Rajaram Samant, Thane-West (IN); Rajendra Prasad Tongra, Jaipur (IN)

(73) Assignee: CELAGENEX RESEARCH (INDIA) PVT. LTD., Thane (IN)

( * ) Notice: Subject to any disclaimer, the term of this patent is extended or adjusted under 35 U.S.C. 154(b) by 0 days.

(21) Appl. No.: 17/336,166

(22) Filed: Jun. 1, 2021

(65) Prior Publication Data
US 2022/0040226 A1 Feb. 10, 2022

(30) Foreign Application Priority Data
Jun. 1, 2020 (IN) .............................. 202021018736

(51) Int. Cl.
*A61K 31/164* (2006.01)
*A61K 31/192* (2006.01)
(Continued)

(52) U.S. Cl.
CPC ............ *A61K 33/06* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 33/00* (2013.01)

(58) Field of Classification Search
None
See application file for complete search history.

(56) References Cited

U.S. PATENT DOCUMENTS

| 4,271,189 A | 6/1981 | Durlach |
| 6,984,484 B1 | 1/2006 | Snyder |

(Continued)

FOREIGN PATENT DOCUMENTS

| EP | 3529229 A1 | 8/2019 |
| JP | 6550426 B2 | 7/2019 |

(Continued)

OTHER PUBLICATIONS

The Recovery Village—Dr. Nicolas Gutierrez, Jan. 2020.
(Continued)

*Primary Examiner* — Lakshmi S Channavajjala
(74) *Attorney, Agent, or Firm* — Maschoff Brennan

(57) ABSTRACT

The invention disclosed herein relates to novel synergistic medicinal compositions for treating dysfunctional D-serine (DSR) signaling. Particularly the invention provides potent synergistic medicinal composition comprising combination of N-acetyl taurinate salt of divalent metal ($M^{2+}AT$) as serine racemase enzyme (SR) activator/stimulator and benzoic acid ester salt of monovalent or divalent metals ($M^{+/2+}Bz$) as d-amino acid oxidase enzyme (DAAO) inhibitor, which are present in weight ratio of 1:0.001 to 1:1.5 along with pharmaceutically acceptable excipients. Further the present synergistic medicinal composition is useful for treating certain neuropsychiatric disorders, neurological disorders and metabolic disorders.

5 Claims, 8 Drawing Sheets

(51) Int. Cl.
*A61P 25/18* (2006.01)
*A61K 33/06* (2006.01)
*A61K 9/00* (2006.01)
*A61K 9/20* (2006.01)
*A61K 33/00* (2006.01)

(56) References Cited

U.S. PATENT DOCUMENTS

| 7,893,098 | B2 | 2/2011 | Fang | |
|---|---|---|---|---|
| 7,902,252 | B2 | 3/2011 | Heffernan | |
| 10,039,730 | B2 * | 8/2018 | Tsai | A61K 31/438 |
| 10,149,845 | B2 | 12/2018 | Tsai | |

FOREIGN PATENT DOCUMENTS

| WO | 2008116226 | A2 | 9/2008 |
|---|---|---|---|
| WO | 2017215592 | A1 | 12/2017 |
| WO | 2017215593 | A1 | 12/2017 |
| WO | 2019072568 | A1 | 4/2019 |
| WO | 2019/209943 | A1 | 10/2019 |

OTHER PUBLICATIONS

Am Fam Physician. Mar. 1, 2010;81(5):617-622.
Biol Psychiatry. May 15, 2007;61(10):1200-3.
PLoS One. Mar. 17, 2016;11(3).
Front Psychiatry. Feb. 5, 2018;9:14.
Trends Neurosci. (2016) 39:712-21.
Proc Natl Acad Sci U S A. Apr. 25, 2000;97(9):4926-31.
Islets. 2016; 8(6): 195-206.
Braz J Psychiatry. Dec. 2006;28(4):301-4.
Scientific Reports vol. 9, Article No. 5104 (2019).
Arch Gen Psychiatry. 2003;60(6):572-576.
Biochim Biophys Acta Proteins Proteom. Apr. 2017;1865(4):381-387.
Alcohol. 1999; 19:119-30.
Uysal et al. 2018 Biological Trace Element Rsearch.

* cited by examiner

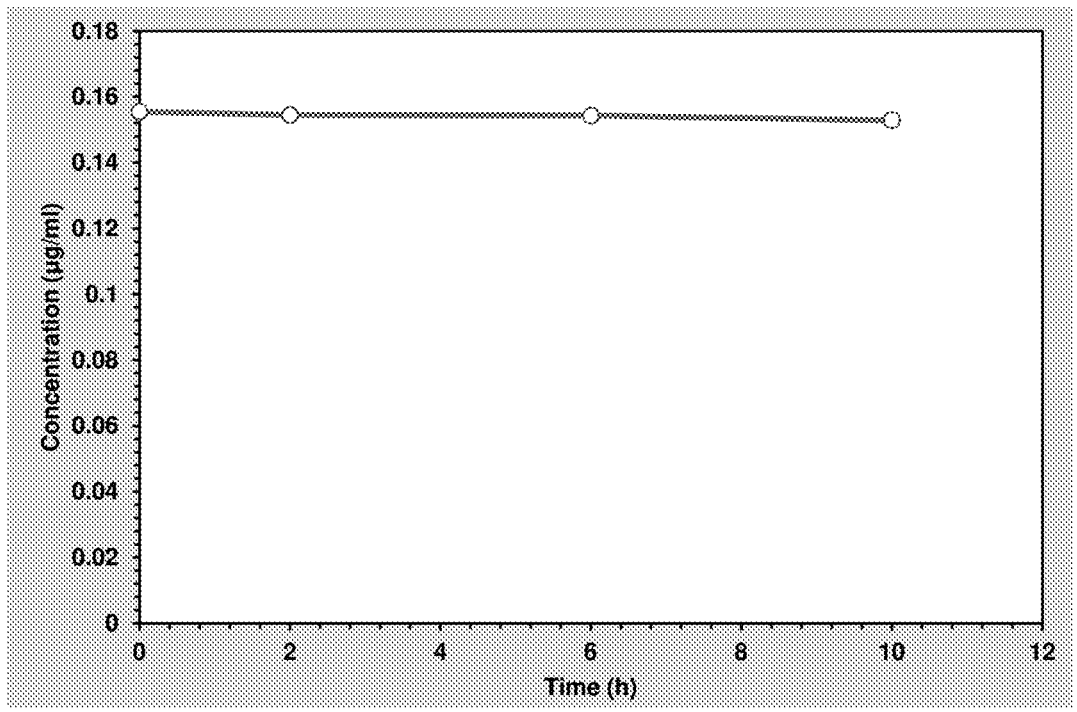
Figure 2 (i)
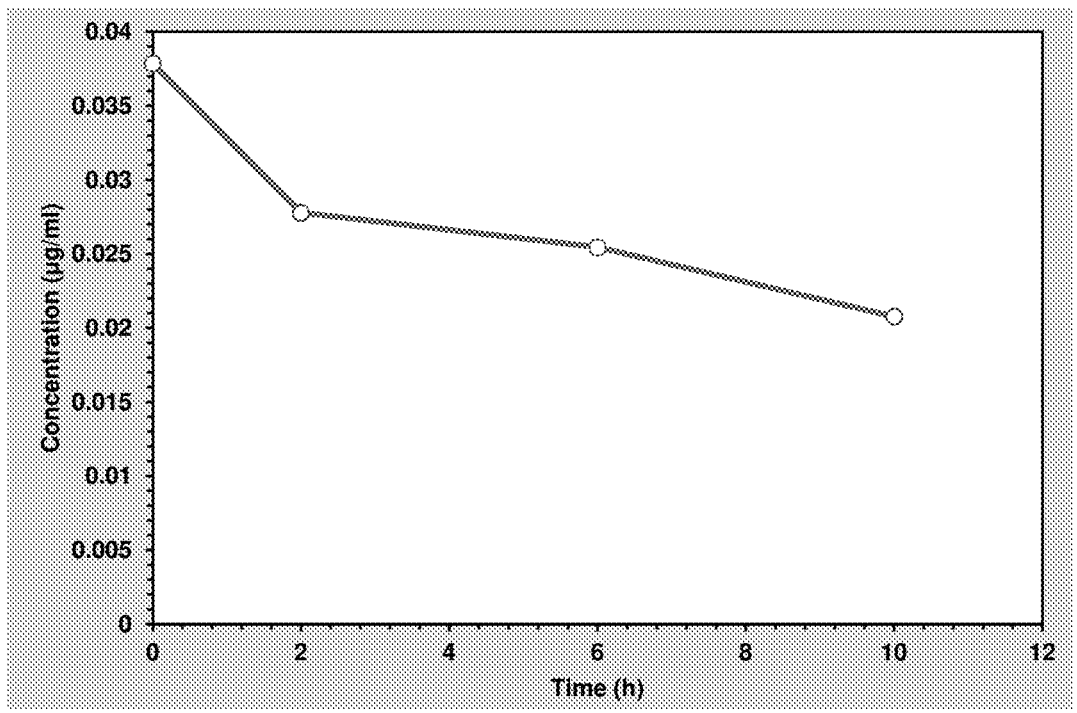
Figure 2 (ii)

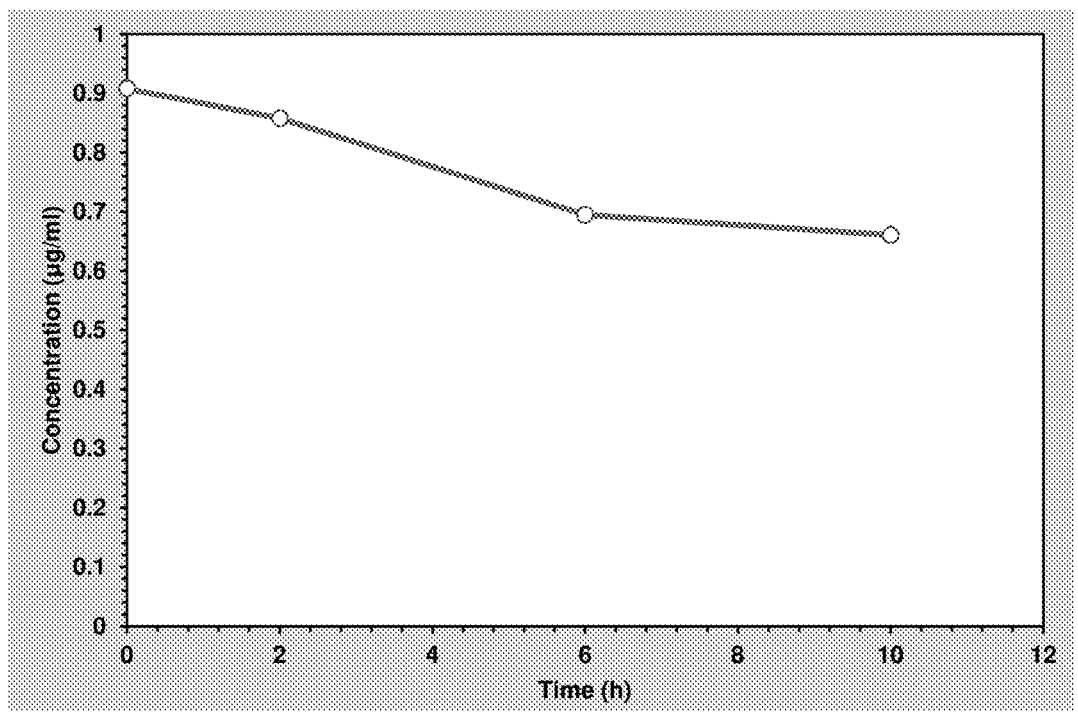
Figure 2 (iii)
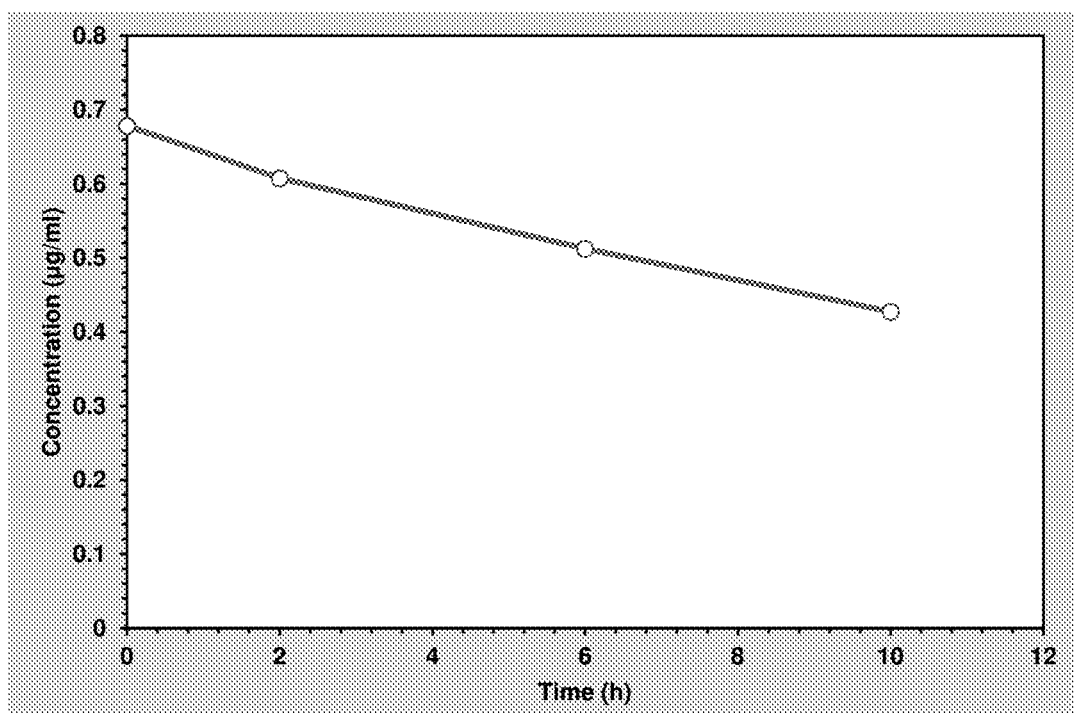
Figure 2 (iv)

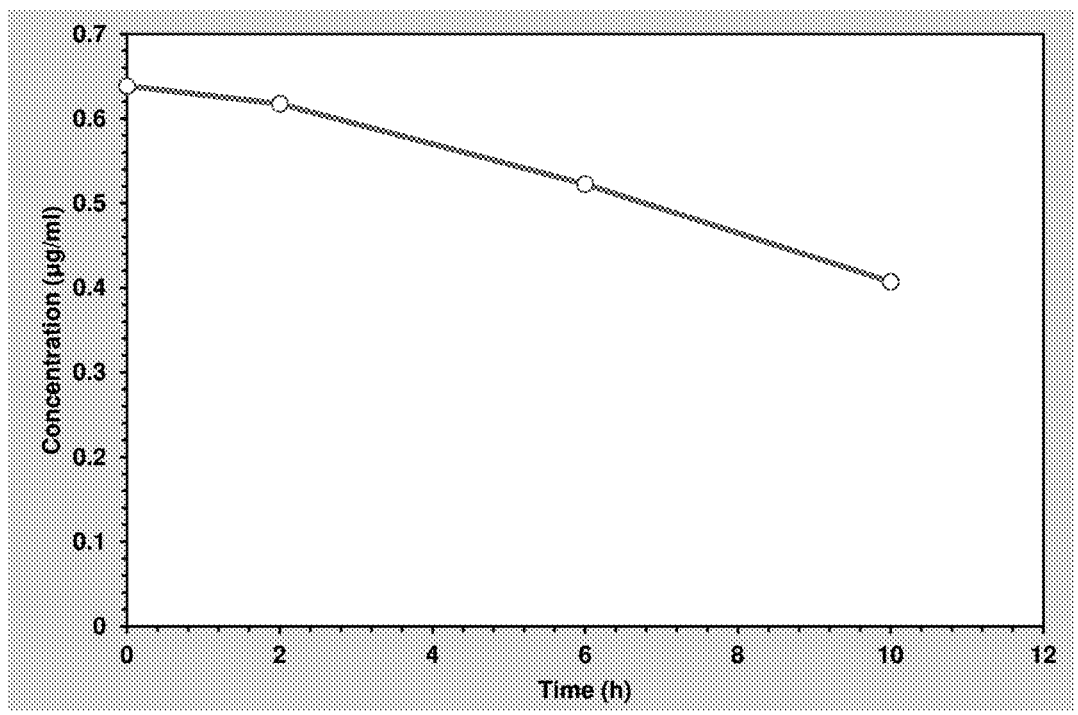
Figure 2 (v)
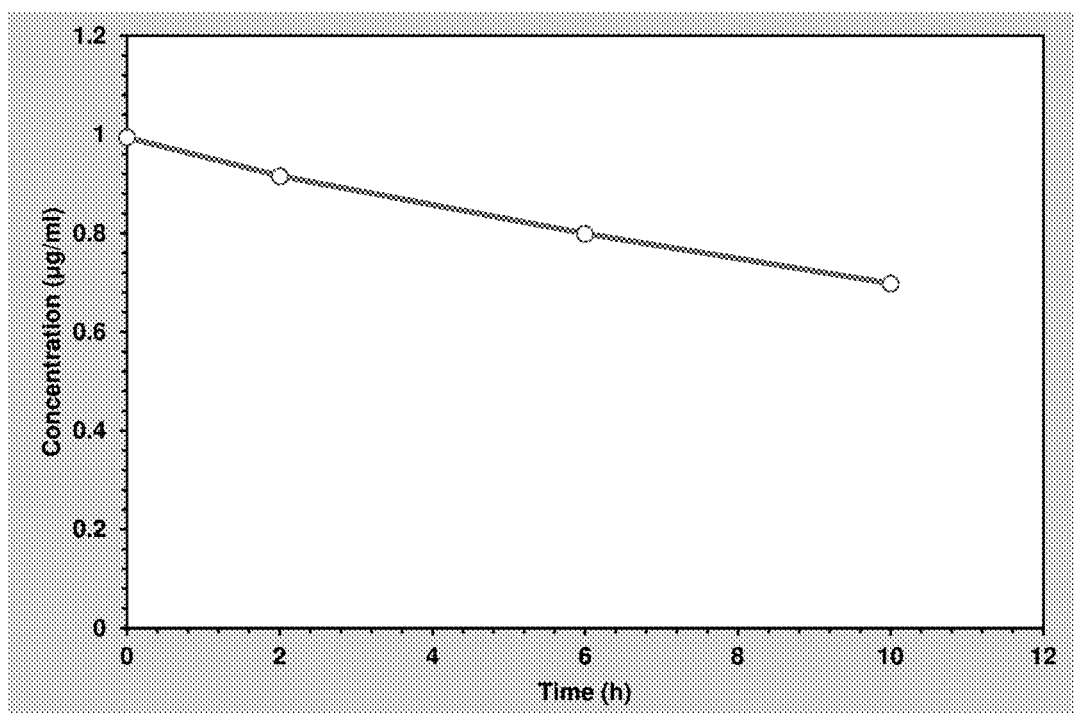
Figure 2 (vi)

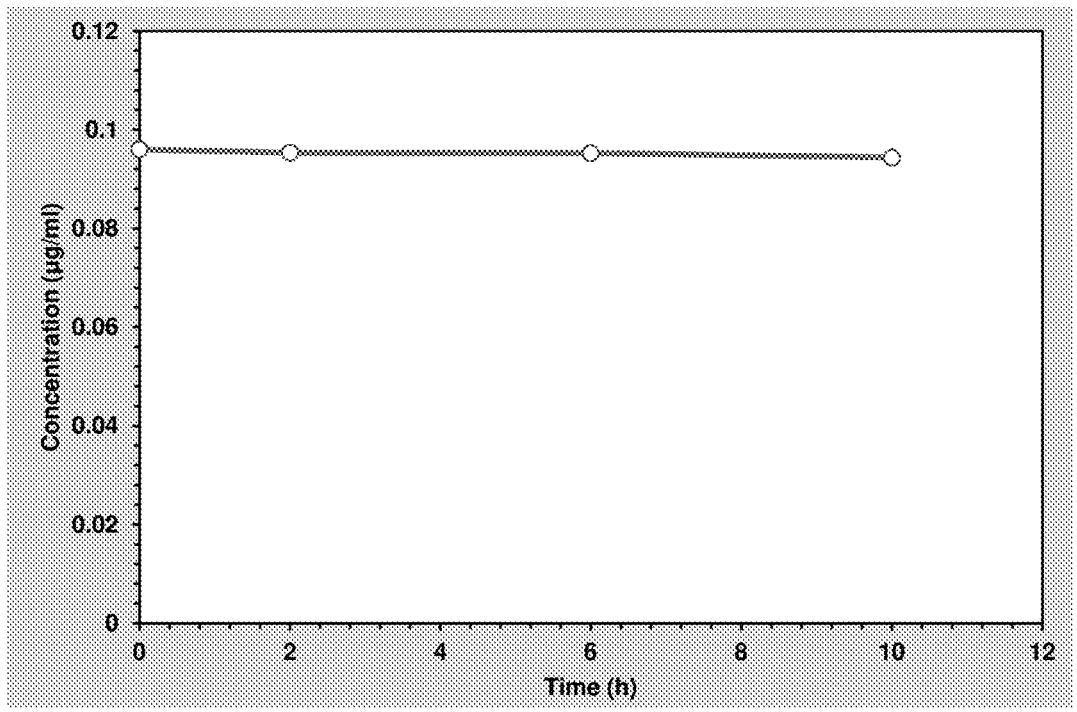
Figure 3 (i)
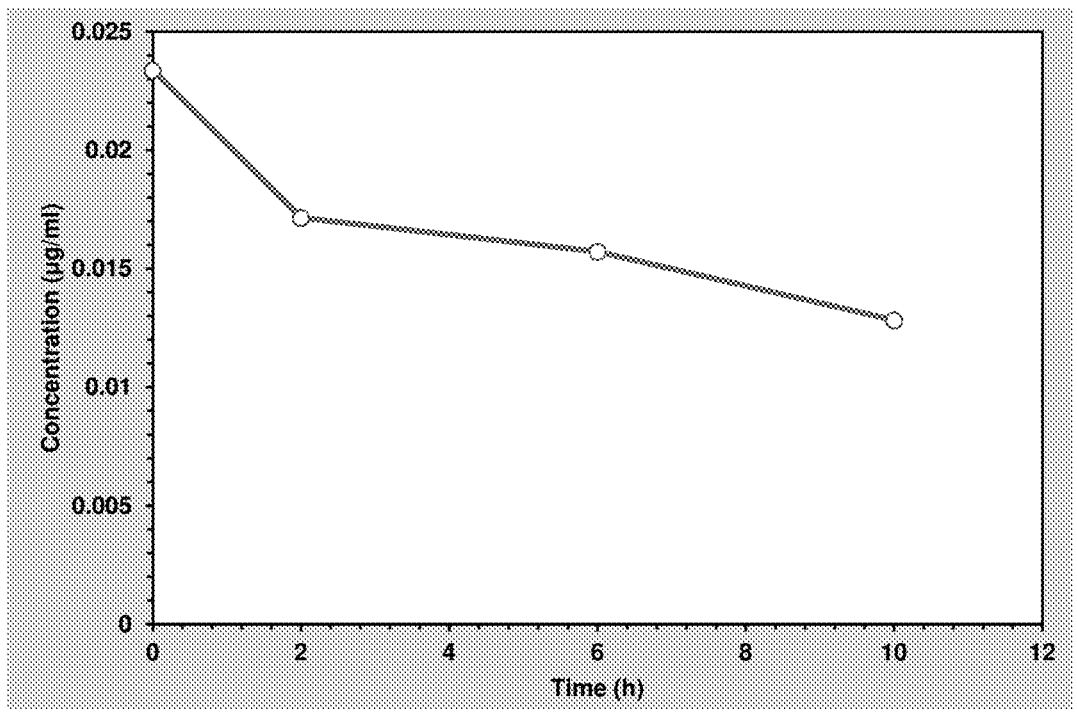
Figure 3 (ii)

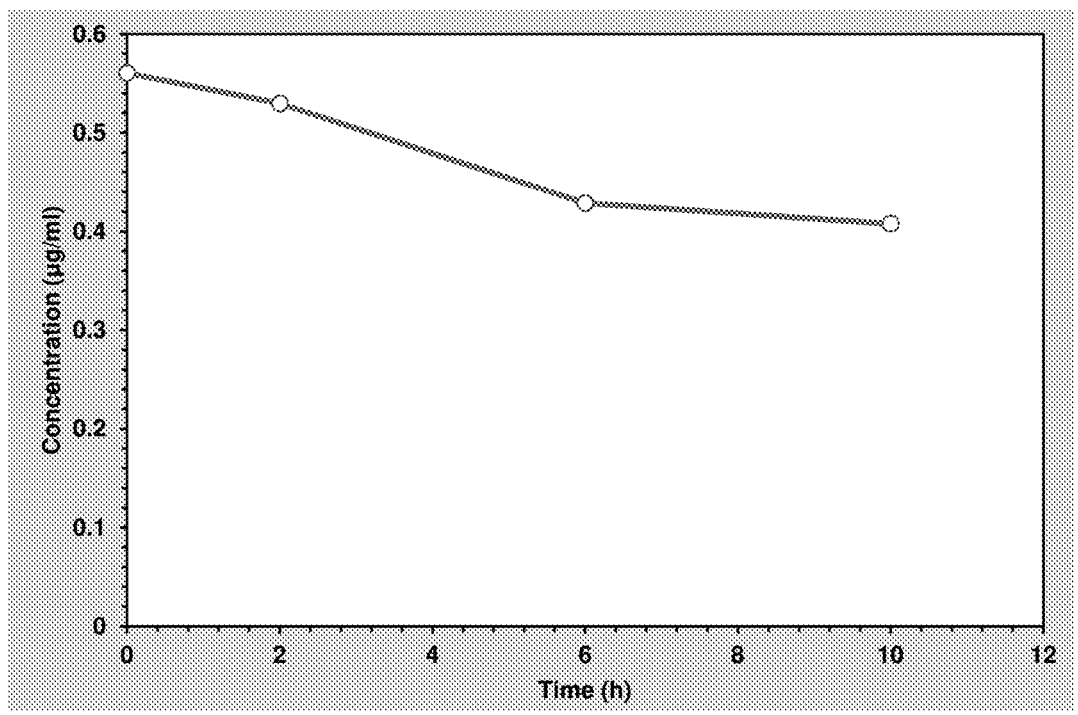
Figure 3 (iii)
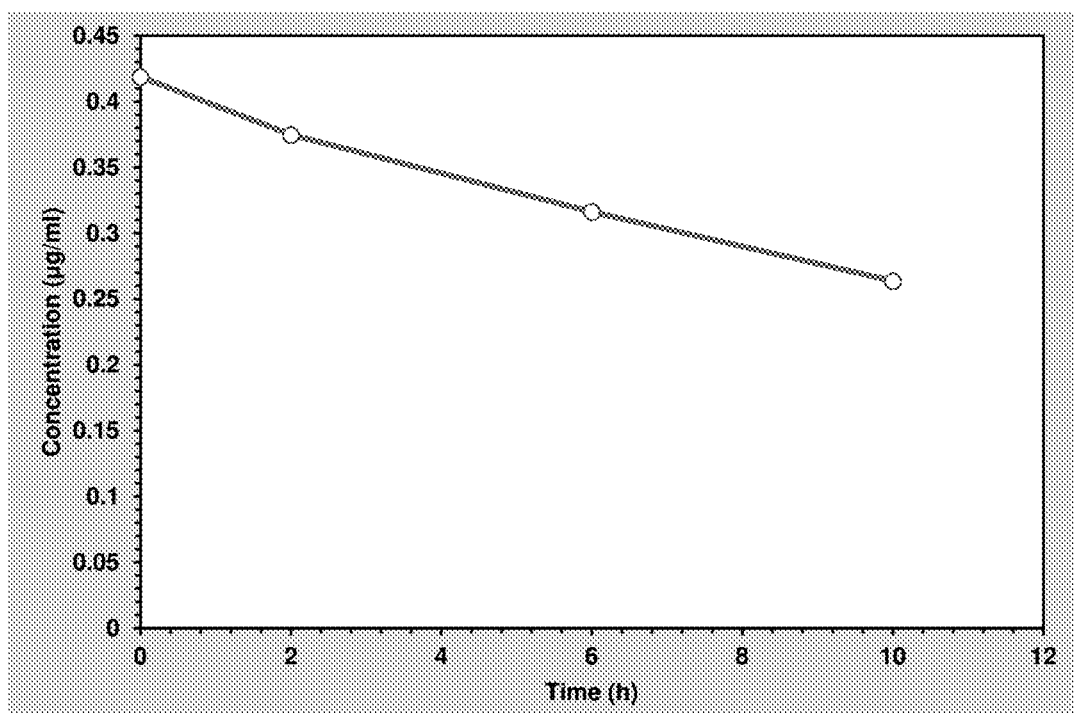
Figure 3 (iv)

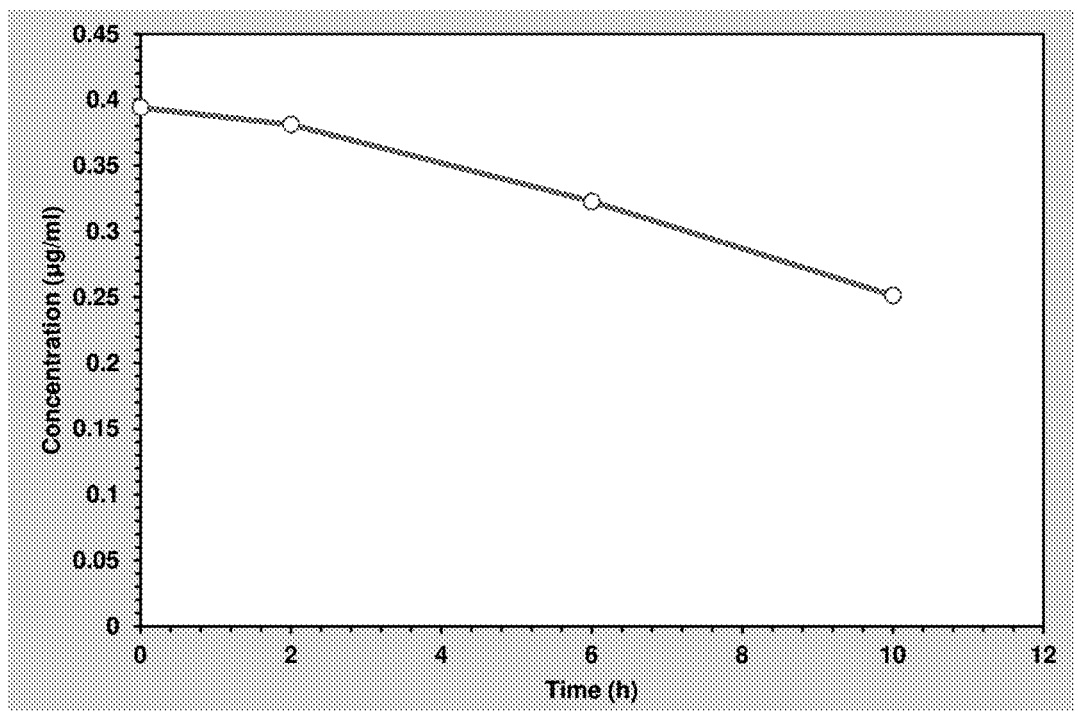
Figure 3 (v)
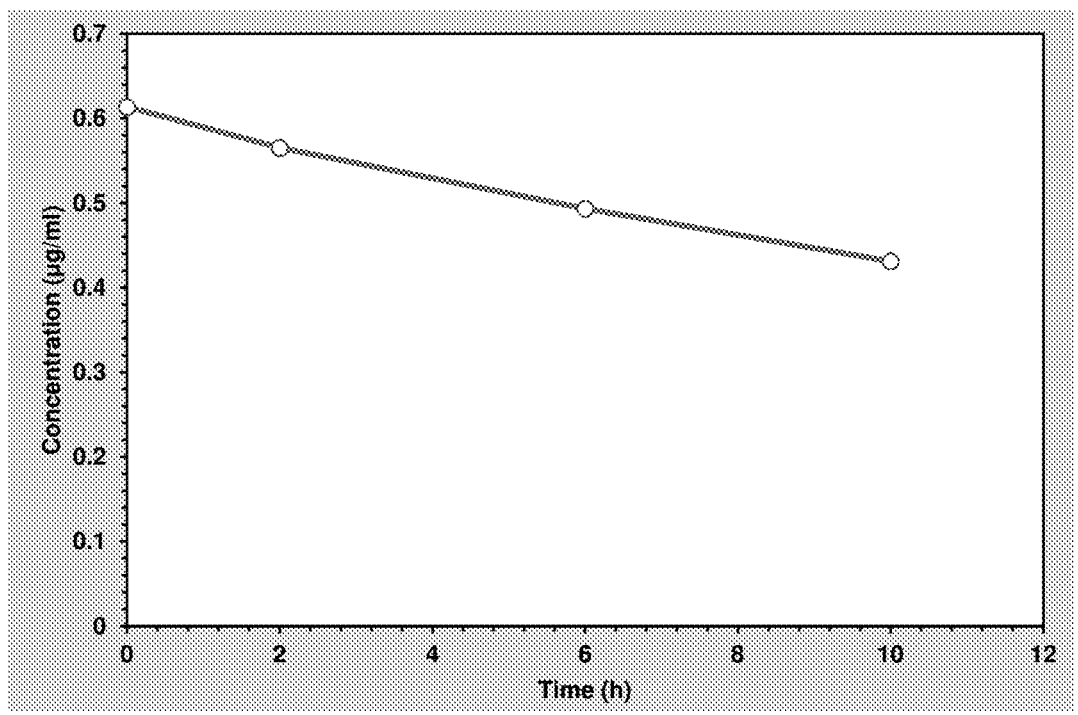
Figure 3 (vi)

SYNERGISTIC MEDICINAL COMPOSITIONS FOR TREATING DYSFUNCTIONAL D-SERINE SIGNALING

FIELD OF THE INVENTION

The present invention relates to novel synergistic medicinal compositions for treating dysfunctional D-serine (DSR) signaling. Particularly, the invention provides potent, synergistic medicinal composition comprising combination of N-acetyl taurinate salt of divalent metal ($M^{2+}AT$) as serine racemase enzyme (SR) activator/stimulator and benzoic acid ester salt of mono valent or divalent metals ($M^{+/2+}Bz$) as d-amino acid oxidase enzyme (DAAO) inhibitor, which are present in suitable weight ratio along with pharmaceutically acceptable excipients. Further, the composition ameliorates D-serine mediated NMDAR signaling pathways in brain, pancreas, liver, adipose tissue, and kidney. Notably, the present medicinal composition is useful for treating certain neuropsychiatric disorders, neurological disorders and metabolic disorders.

BACKGROUND OF THE INVENTION

Psychosis is characterized by an impaired relationship with reality. It is a symptom of serious mental disorder. Psychosis distorts a person's perceptions and thoughts through hallucinations (hearing or seeing things that are not real) and delusions (holding strange beliefs). While psychosis is often a feature of psychotic disorders, it can also occur without the presence of any mental health condition.

Psychosis is often described as a "loss of reality" or a "break from reality" because it makes experience or believe things that aren't real. In fact, the World Health Organization (WHO) ranks psychosis as the third-most disabling medical condition in the world. According to recent statistics, by *The Recovery Village*—Dr. Nicolas Gutierrez, January 2020, it is observed that around 3% of the people of the United States experience at least one psychotic episode during their lives. Every year, about 100,000 teenagers and young adults in the United States experience their first psychotic episode. Psychotic disorder statistics estimate that between 0.25 and 0.64% of the people in the U.S. suffer from a psychotic disorder.

While schizophrenia is the most common psychotic disorder, several other mental health conditions also fall into this category. Other psychotic disorders include schizoaffective disorder, schizophreniform disorder, delusional disorder, brief psychotic disorder and substance-induced psychosis. Other mental health conditions, including bipolar disorder and depression, may also feature symptoms of psychotic disorders.

Psychosis can be related to several conditions, such as manic depressive psychosis (also known as bipolar psychosis). Bipolar disorder, which is characterized by dramatic shifts from high (mania) to low mood (depression), can also trigger psychotic episodes. Bipolar disorder affects around 2.6% of the people in the United States, but it is much harder to establish the prevalence of psychosis in bipolar disorder because it tends to be mistaken for schizophrenia. Depression and psychosis may also occur during episodes of severe depression. Research shows that around 14% of people with severe depression had a history of psychotic features.

Psychosis can also occur after childbirth. Postpartum psychosis statistics show that 1-2 out of 1000 births result in psychosis, often during the first four weeks after the delivery. Psychotic disorders increase the risk of suicidal tendencies, particularly for people living with schizophrenia. According to several studies, between 5 and 10% of people with schizophrenia commit suicide, compared to 10 per 100,000 in the general population.

Antipsychotics, also known as neuroleptics, are a class of medication primarily used to manage psychosis (including delusions, hallucinations, paranoia or disordered thought), particularly in schizophrenia and bipolar disorder. The long-term use of antipsychotics may result in adverse effects such as involuntary movement disorders, gynecomastia, impotence, weight gain and metabolic syndrome. All antipsychotic medications are associated with an increased likelihood of sedation, sexual dysfunction, postural hypotension, cardiac arrhythmia, and sudden cardiac death.

The use of antipsychotic medications entails a difficult trade-off between the benefit of alleviating psychotic symptoms and the risk of troubling, sometimes life-shortening adverse effects. There is more variability among specific antipsychotic medications than there is between the first- and second-generation antipsychotic classes [*Am Fam Physician.* 2010 Mar. 1; 81(5):617-622].

The administration of first-generation neuroleptics typically butyrophenones, diphenylbutylpiperidines, phenothiazines, thioxanthenes, tricyclics class drugs encounter with adverse effects like tardive dyskinesia, akathisia, metabolic syndrome, seizures, stroke myocardial infarction, dystonic reactions. Many of the atypical drugs are more likely to contribute to metabolic side effects such as weight gain, increased glucose and lipids.

The newer second-generation antipsychotics, especially clozapine and olanzapine, generally tend to cause more problems relating to metabolic syndrome, such as obesity and type 2 diabetes mellitus. Therefore, the unmet need arises to find out alternative ingredients which are therapeutically effective without any severe side effects.

Advancement in neuroimaging, cell biology, and post mortem analysis explain that a brain of a person who develops psychosis such as schizophrenia appears to be a developmental disorder of disrupted neural connection within and between regions of the brain. These disruptions seem to result from irregularities in synaptic density, neurotransmission, apoptosis, necrosis, motor function due to dysregulation of certain optically active amino acids.

D-serine was the second D-amino acid discovered to naturally exist in humans. The first one was D-aspartate. D-serine is synthesized from L-serine by serine racemase (SR), and it is degraded by D-amino acid oxidase (DAAO). It is found in high abundance in the brain. The results of research from large-scale genomic studies suggest that genetic variation has a major influence on a broad range of psychiatric disorders. Many risk loci have already been identified through genome-wide association studies (GWAS) for disorders spanning schizophrenia (SCZ), bipolar disorder (BIP), major depression (MD), and attention-deficit/hyperactivity disorder (ADHD). Identifying which gene variants increase the odds for developing multiple psychiatric disorders provides new clues about the biological pathways that contribute to mental illness.

Notably, it is found that a genetic variant of serine racemase (SR) and D-amino acid oxidase (DAAO) gene are associated with neurocognitive functions in schizophrenia [*Biol Psychiatry.* 2007 May 15; 61(10):1200-3] [*PLoS One.* 2016 Mar. 17; 11(3)]. These genes may play a vital role in the pathophysiology of schizophrenia.

The present inventors have surprisingly observed that modulation of these two specific genes or enzymes SR and DAAO gives favourable results in DSR signalling. With extensive research in animal brain, it is found that D-serine is one of the prime modulators of synaptic plasticity and cognitive functions, which processes through its actions on the NMDA-glutamate receptor. Significantly, cognitive impairment is a core feature of conditions, such as schizophrenia, Alzheimer's disease, depression, and ageing, and is associated to disturbances in NMDA-glutamate receptors. The D-serine pathway has been associated with cognitive deficits and conditions that trigger psychotic episodes. [Front Psychiatry. 2018 Feb. 5; 9:14].

D-serine participates in multiple processes, including synaptic plasticity, cell migration, synaptogenesis and in homeostatic functions, as a mediator of hypercapnia-induced respiratory response. D-serine production and release is appeared to be closely regulated, and its concentration is maintained in a narrow range. Dysregulation of D-serine may lead to pathology. Abnormally increased levels of D-serine are associated with NMDAR-mediated neurotoxicity whereas abnormally decreased levels are associated with impairments in functional plasticity and memory deficits.

Consequently D-serine signaling is subject of intense research to probe its role in aiding diagnosis and therapy. Therefore, the inventors of the present invention identified the pathways, regarding D-serine pharmacokinetics, to modulate its levels, and synergistic effect to increase its efficacy. An increasing amount of evidence indicates that D-serine, a potent and selective endogenous coagonist of the N-methyl-D-aspartate receptor (NMDAR), is efficacious in the treatment of schizophrenia. Although the therapeutic efficacy of D-serine supplementation is based on the D-serine deficit and NMDAR hypofunction hypothesis, it is manifested that D-serine levels are decreased in patients with schizophrenia compared to healthy controls.

Either over or underfunction of NMDAR neurotransmission may elicit neurotoxicity, leading to behavioral and cognitive dysfunction. NMDAR hyperactivity can cause cell death mediated by excitotoxic calcium overload in stroke and neurodegenerative disorders such as Alzheimer's disease (AD). By contrast, synaptic NMDAR hypoactivity leads to apoptosis and may contribute to the generation of psychotic symptoms and cognitive deficits. Because D-serine is such a potent coagonist at the NMDA receptor, there has been a great deal of interest in its role in the brain. D-serine is present in glia (mainly astrocytes) and neurons. It has been proposed as both a glial transmitter and a neurotransmitter.

Wolosker et al. have proposed that astrocytes synthesize L-serine which then shuttles to neurons to be converted to D-serine [Trends Neurosci. (2016) 39:712-21]. D-serine (DSR) is an endogenous amino acid involved in glia-synapse interactions that has unique neurotransmitter characteristics. DSR acts as obligatory coagonist at the glycine site associated with the N-methyl-D-aspartate subtype of glutamate receptors (NMDAR) and have a cardinal modulatory role in major NMDAR-dependent processes including NMDAR-mediated neurotransmission, neurotoxicity, synaptic plasticity, and cell migration. Since either over- or underfunction of NMDARs may be involved in the pathophysiology of neuropsychiatric disorders; the pharmacological manipulation of DSR signaling represents a major drug development target. A first generation of proof-of-concept animal and clinical studies suggest beneficial DSR effects in treatment-refractory schizophrenia, movement, depression, and anxiety disorders and for the improvement of cognitive performance. A related developing pharmacological strategy is the indirect modification of DSR synaptic levels by use of compounds that alter the function of main enzymes responsible for DSR production and degradation.

D-serine is synthesized in neurons by serine racemase from L-serine (its enantiomer), serves as a neuromodulator by coactivating NMDA receptors, making them able to open if they then also bind glutamate. D-serine is a potent agonist at the glycine site (NR1) of the NMDA-type glutamate receptor (NMDAR). In fact, D-serine is a more potent agonist at the glycine site on the NMDAR than glycine itself [Proc Natl Acad Sci USA. 2000 Apr. 25; 97(9):4926-31].

U.S. Pat. No. 6,984,484B1 discloses process for purification of serine racemase which is useful for treating conditions and diseases that involve overstimulation of NMDA receptors, such as stroke and various neurodegenerative diseases.

Apart from central nervous system, D-serine plays a signaling role in peripheral tissues and organs such as cartilage, adipose, kidney, liver, pancrease and corpus cavernosum.

Serine racemase is expressed in islets and contributes to the regulation of glucose homeostasis [Islets. 2016; 8(6): 195-206]. The metabolic actions of D-serine could contribute strong linkage between obesity, T2D, dyslipidemia, and schizophrenia [Braz J Psychiatry. 2006 December; 28(4): 301-4]. D-serine may serve as a vital biomarker that suppress CKD onset through the precise assessment of kidney function and the diagnosis of CKD [Scientific Reports volume 9, Article number: 5104 (2019)].

Reduced levels of D-serine may play a role in the pathophysiology of schizophrenia, and serum D- and L-serine levels might provide a measurable biological marker for schizophrenia [Arch Gen Psychiatry. 2003; 60(6):572-576]. D-serine is an allosteric modulator of the brain N-methyl-D-aspartate (NMDA) receptor and a potential productive treatment of schizophrenia. D-serine, an obligatory co-agonist at the NMDA receptor, is integral to neurotransmission via NMDA signaling throughout development and into adulthood. D-serine is used to potentiate NMDA receptor-mediated neurotransmission, it is more permeable than glycine to the blood-brain barrier.

A number of clinical studies have highlighted disturbed NMDA receptor neurotransmission due to decreased D-serine levels as a causative factor in the pathophysiology of psychosis. Mammalian serine racemase is a pyridoxal 5'-phosphate dependent enzyme that catalyzes both the racemization of L-serine to D-serine and also the elimination of water from L-serine, generating pyruvate, $H_2O_2$ and ammonia. The enzyme is physiologically stimulated or allosterically activated by free divalent cations or its ATP complex.

Further it is observed that production of ROS like $H_2O_2$ during elimination reaction trigger neuroinflammation, oxidative stress and excitotoxicity that results in cell damage or necrosis. Serine racemase (SR) is the pyridoxal 5'-phosphate dependent enzyme that catalyzes both production and catabolism of d-serine, a co-agonist of the NMDA glutamate receptors. $Mg^+$, or, alternatively, $Ca^{2+}$, activate human serine racemase by binding both at a specific site and as ATP-metal complexes at a distinct ATP binding site. The co-presence of ATP and metals stabilizes the tetramer of SR [Biochim Biophys Acta Proteins Proteom. 2017 April; 1865(4):381-387]. The initial rates of racemization and α,β-elimination of L-serine by serine racemase are strongly stimulated by magnesium and ATP, indicating that the complex Mg.ATP is a physiological ligand of the enzyme.

Psychoses are amongst the most severe diseases of the CNS. Various neurological and psychiatric pathologies are associated with changes of plasma and intracellular magnesium and other bivalent cations. Such changes in magnesium concentrations have been observed in brain injury, stroke, headaches, epilepsy, major depression and others [*Alcohol.* 1999; 19:119-30]. Schizophrenia and bipolar psychosis present an increasing incidence.

Advantageously, serine racemase activity in the presence of divalent cations is enhanced. It is best metal ion cofactor in enzymatic systems. Therefore, a need springs up to evaluate more potent and highly bioavailable salt of divalent cations like $Mn^{2+}$, $Mg^{2+}$ and $Ca^{2+}$. In prior art, various types of Mg salts are available which shows efficacy and bioavailability such as WO2019/209943A1 provides magnesium threonate dosage for the treatment of mild cognitive impairment, short-term memory loss, long term memory loss, Alzheimer's disease, Parkinson's disease, Huntington's disease, autism, schizophrenia, cognitive decline, depression, and dementia.

Further, WO2008116226A2 discloses magnesium-comprising component (MCC) such as magnesium acetate, magnesium ascorbate, magnesium citrate, magnesium gluconate, magnesium lactate, magnesium malate, magnesium pyrrohdone carboxylate, magnesium taurate, and magnesium threonate, and at least one component of non-acidified milk sufficient to enhance bioavailability of elemental magnesium associated with the MCC, for treating neurological disorders like Alzheimer's disease, and depression.

However, the role of these salts in D-serine pathway is not demonstrated in the said publications. Thus, the present inventors come up with hitherto unexploited divalent metal salt which not only improves rate of racemization by stimulating SR but also attenuates neurotoxicity caused due to eliminated ROS. N-acetyl-taurinate salts of divalent metals are highly bioavailable and soluble form of metals salts. Particularly magnesium acetyl taurate is rapidly absorbed, and able to pass through to the brain easily, it has the highest tissue concentration level in the brain, and found to be associated with decreased anxiety indicators. Further, magnesium taurate levels remained high for a long time in the serum [Uysal et al. 2018 *Biological Trace Element Rsearch*].

WO2019072568A1 discloses use of magnesium N-acetyl-taurinate for improving neuronal plasticity in the treatment of neurological conditions such as epilepsy, Parkinson's disease, Alzheimer's disease and amyotrophic lateral sclerosis. Further, U.S. Pat. No. 4,271,189 describes metal derivatives of acetyl taurinate for treating manic-depressive psychosis. However the role of Mg acetyl taurinate in D-serine pathway is not disclosed in the prior arts.

Notably, DSR has a cardinal modulatory role in major NMDAR-dependent processes, including NMDAR neurotransmission, neurotoxicity, synaptic plasticity, and cell migration. The long standing paradox that NMDARs can both promote neuronal health and kill neurons highlights the importance of a strictly regulated optimal NMDAR function. In this context DSR modulation appears to play a critical role in the achievement of balanced NMDAR activity. Furthermore, compelling evidence suggests that dysfunctional DSR signaling may be involved in the pathophysiology of neuropsychiatry disorders.

In animals, D-serine is synthesized by isomerization of L-serine, in a reaction catalyzed by the enzyme serine racemase. Mere regulating isomerization or enhancing rate of racemization from L serine to D-serine is not enough to upregulate the concentration of D-serine at NMDAR sites as D-serine is preferentially degraded through oxidation by the enzyme called D-amino acid oxidase DAAO and also by the serine racemase-mediated water $\alpha,\beta$-elimination induced by elevated intracellular D-serine levels.

D-amino acid oxidase (DAAO); also known as OXDA, DAMOX is an enzyme with the function on a molecular level to oxidize D-amino acids to the corresponding imino acids, producing ammonia and hydrogen peroxide. DAAO in humans play a role in the glutamatergic mechanisms of schizophrenia.

D-amino acid oxidase (DAAO) is a flavoenzyme that degrades D-amino acids through the process of oxidative deamination. DAAO regulation of D-amino acid levels has been associated with several physiological processes Because NMDA receptor dysfunction is thought to be involved in the positive (psychotic), negative and cognitive symptoms in schizophrenia, there has been much interest in developing potent and selective DAAO inhibitors for the treatment of this disease. Several research reports have been published that describe the synthesis and biological effects of novel, selective, small molecule inhibitors of DAAO. Regulation of NMDA receptor co-agonists through the pharmacological manipulation of DAAO and glycine transporters (GlyT1) has been investigated as putative novel therapeutics to treat schizophrenia.

Taken together, these finding suggest that DAAO inhibitors might be useful as potent therapeutics to treat psychiatric and cognitive disorders. Inhibition of the enzyme D-amino acid oxidase (DAAO) represents a new mechanism for enhancing DSR and ultimately NMDAR signaling.

Benzoate salts of metal ions are commonly used food preservative, which also exhibit DAAO inhibition activity with good CNS bioavailability. Further, neurocognition can be improved by benzoate salts.

U.S. Ser. No. 10/149,845B2 discloses use of a DAAOI such as a benzoic acid, benzoic acid salt, benzoic acid ester or other benzoic acid derivative and/or sorbic acid, a sorbic acid salt, a sorbic acid ester or other sorbic acid derivative for improvement in subjects diagnosed with neuropsychiatric disorders. Small organic molecules, which inhibit the enzymatic cycle of DAAO, can be used to control the levels of D-serine, and thus can influence the activity of the NMDA receptor in the brain. DAAO inhibitors can also control production of toxic metabolites of D-serine oxidation, such as hydrogen peroxide and ammonia where these molecules can influence the progression of cell loss in neurodegenerative disorders.

The toxicology of benzoate administration has been studied extensively and exhibits good safety margins. Benzoic acid and its salts are known and used as food preservatives represented by the E-numbers E210 to E213. Concentration as a preservative is limited by the US Food and Drug Administration to 0.1% by weight. The World Health Organization (WHO) suggests a provisional tolerable intake of 5 mg/kg daily. It is believed that the DAAOI enhances the levels of both D-serine a co-agonists of NMDA receptor and beneficial for patients with schizophrenia and other psychotic disorders.

JP6550426B2 discloses sodium benzoate as an inhibitor of DAAO, for treating cognitive impairment or dementia. Further, WO2017215593A1 and EP3529229A1 provide co-crystals and polymorphic forms of sodium benzoate respectively for treating and/or reducing the risk for a neuropsychiatric disorder (e.g., schizophrenia, psychotic disorders, depressive disorders, or Alzheimer's disease) or a glucose or lipid metabolic disorder (e.g., obesity, diabetes, hypercholesterolemia, hypertension, or hyperlipidemia).

Additionally, WO2017215592A1 unwraps co-crystals of a lithium benzoate compound for treating and/or reducing the risk for a neuropsychiatric disorder (e.g., schizophrenia, psychotic disorders, depressive disorders, bipolar disorders, or neurodegenerative disorders).

U.S. Pat. No. 7,893,098B2 and U.S. Pat. No. 7,902,252B2 discloses pyrrole and pyrazole derivatives that exhibit potent inhibition of DAAO activity where they reduce concentration of the toxic products of D-serine oxidation, for enhancing learning, memory and/or cognition, or for treating schizophrenia, Alzheimer's disease, ataxia or neuropathic pain. Overall, benzoate treatment gives rise to a favorable profile of improvement in principal psychotic symptoms and neurocognition. Inhibition of DAAO (e.g., by benzoate treatment) represents a novel therapeutic target for the development of new pharmacotherapy for the clinical efficacy and improvement of life functioning in patients with schizophrenia.

In view of the critical role of D-serine optimization for regulating NMDAR activity it is necessary to establish additional, alternative therapeutic approach, that involves GRAS or EFSA regulated food ingredients as active nutrients for ameliorating DSR signaling pathway without general neuroleptics side effects. Surprisingly, the inventors of present invention have developed synergistic combination of non-neuroleptics classified therapeutically active and safe ingredients for ameliorating DSR concentration by improving rate of racemization from LSR to DSR and simultaneously inhibiting degradation of DSR thus maintains the optimum level of DSR for better CNS and PNS functioning.

OBJECTIVES OF THE PRESENT INVENTION

The primary objective of the invention is to provide synergistic medicinal compositions for treating dysfunctional D-serine (DSR) transmission/signaling.

Another objective of the invention is to provide synergistic medicinal compositions for ameliorating D-serine mediated NMDAR activation.

Further objective of the present invention is to provide promising therapeutic approach for induction of serine racemase expression and D-serine release from microglia.

Other objective of the invention is to provide therapeutically-effective, cost-effective, and side-effect-free alternative to antipsychotics/antineuropsychiatrics for a subject in need thereof.

Further objective of the invention is to provide combination of therapeutically active, non toxic, generally recognised as safe chemical substances/ingredients for enhancing deficit D-serine.

Some other objective of the invention is to provide combination of therapeutically active, medicinal ingredients that work synergistically to maintain optimum/regulated DSR.

Yet another objective of the invention is to provide therapeutically effective, safe, natural remedy for treating neuropsychiatric, neurological and metabolic disorder caused due to depletion of D-serine levels.

SUMMARY OF THE PRESENT INVENTION

To meet the above objectives, the inventors of the present invention carried out thorough experiments to establish significant effect of the bioactive ingredients or food ingredients or nutrients or chemical substances or naturally safe agents present in the composition that ameliorate DSR expression at NMDAR.

In particular aspect, the invention relates to synergistic medicinal compositions comprising therapeutically active food ingredients along with pharmaceutically acceptable carriers for treating dysfunctional D-serine transmission/signaling.

In another particular aspect, the invention provides novel synergistic medicinal compositions comprising synergistic combination of N-acetyl taurinate salt of divalent metal cations ($M^{2+}AT$) as serine racemase enzyme (SR) activator/stimulator; and benzoic acid ester salt of mono valent or divalent metals ($M^{+/2+}Bz$) as D-amino acid oxidase enzyme (DAAO) inhibitor which are present in suitable weight ratio along with pharmaceutically acceptable excipients, wherein $M^{2+}AT$ is N-acetyl taurinate salt of divalent metal cations like $Mg^{2+}$, $Zn^{2+}$ $Mn^{2+}$ and $Ca^{2+}$; and $M^{+/2+}Bz$ is benzoate salt of mono valent or divalent metal cations like $Na^{2+}$, $K^{2+}$, $Mg^{2+}$ and $Ca^{2+}$.

In another aspect, the present invention provides water soluble-food ingredient based synergistic medicinal compositions for regulating D-serine-mediated NMDAR signaling, including regulation of DSR biosynthesis from LSR and its mechanism of release.

In yet another aspect, the invention provides novel medicinal composition for ameliorating endogenous amino acid D-serine (DSR) level comprising specific combination of N acetyl taurinate salt of divalent metals and benzoate salt of mono/divalent metal, wherein monovalent metals are Na, K and divalent metals are Mg, Ca which are present either alone or in combination thereof.

In particular aspect, the present invention provides medicinal neuropsychiatric remedy comprising synergistic combination of magnesium acetyl taurate (MgAT) and sodium benzoate (NaBz) which are present in specific weight ratio, along with pharmaceutically acceptable carriers.

In further aspect, the present invention provides novel and potent medicinal composition, wherein the active moieties perform synergistically to regulate DSR signaling, wherein MgAT induces or activates the expression of serine racemase enzyme; concomitantly NaBz prevents/inhibits D-serine degradation/oxidation that also leads to reduction in neurotoxins such as $H_2O_2$ and ammonia. Further the taurinate salt of metal act as ROS scavenger to attenuate neuroinflammation and stress induced by DSR degradation. Thus the synergistic effect promotes DSR mediated NMDAR signaling.

In another aspect, the invention provides cost effective, non-toxic, efficient and environmentally safe, exogenous medicinal composition comprising synergistic combination of generally recognized as safe chemical substances for maintaining optimum DSR as coagonist for NMDAR activity without severe side effects that are generally related to antipsychotics/antineuropsychiatric drugs.

In yet another aspect, the invention relates to synergistic medicinal compositions comprising combination of N-acetyl taurinate salt of divalent cations ($M^{2+}AT$), which is present in the range of 1 to 5000 mg, containing 1-500 mg of elemental metal; and benzoate salt of mono valent or divalent cations ($M^{+/2+}Bz$) is present in the range of 1 to 3000 mg along with pharmaceutically acceptable excipients/carriers, optionally in presence of bioenhancer.

In yet one more aspect, the invention provides synergistic medicinal composition which is useful for treating neuropsychiatric disorders such as schizophrenia, schizophreniform disorder, brief psychotic disorder, delusional disorder, schizotypal personality disorder, major depressive disorder, bipolar disorder, chronic hallucinatory psychosis, dissociative disorders, obsessive-compulsive disorder, induced delusional disorder, post-traumatic stress disorder, menstrual psychosis, cycloid psychosis and like thereof; neurological disorders such as epilepsy, Alzheimer disease, dementias, stroke, migraine, headache disorders, multiple sclerosis, Parkinson's disease, neuroinfections, traumatic disorders; metabolic disorders such as overweight, abdominal obesity, high blood pressure, high blood sugar, type 2 diabetes (T2D).

ABBREVIATIONS

SR: Serine Racemase
DSR: D-Serine
LSR: L-Serine
WAT: Divalent metal n-acetyl taurinate
$M^{+/2+}Bz$: Mono valent and divalent metal benzoic acid esters
MgAT: Magnesium Acetyl Taurate
NaBZ: Sodium Benzoate
NMADR: N-methyl-D-aspartate receptor
DAAO/DAO: D-amino acid oxidase
PLP/P5P: Pyridoxal 5'-Phosphate

BRIEF DESCRIPTION OF THE DRAWINGS

FIG. 2 illustrates Pharmacokinetics-Area under the plasma blood concentration time curve (AUC) 2(*i*): Plasma Normal Control, 2(*ii*): Disease Control, 2(*iii*): Reference standard, 2(*iv*): Test 1 [MgAT], 2(*v*): Test 2 [NaBz], 2(*vi*): Test 1+Test 2 [MgAT+NaBz].

FIG. 3 illustrates Pharmacokinetics-Area under the plasma brain tissue concentration time curve (AUC) 3(*i*): Brain Tissue Normal Control, 3(*ii*): Disease Control, 3(*iii*): Reference standard, 3(*iv*): Test 1 [MgAT], 3(*v*): Test 2 [NaBz], 3(*vi*): Test 1+Test 2 [MgAT+NaBz].

DETAILED DESCRIPTION OF THE INVENTION

Figure 1:
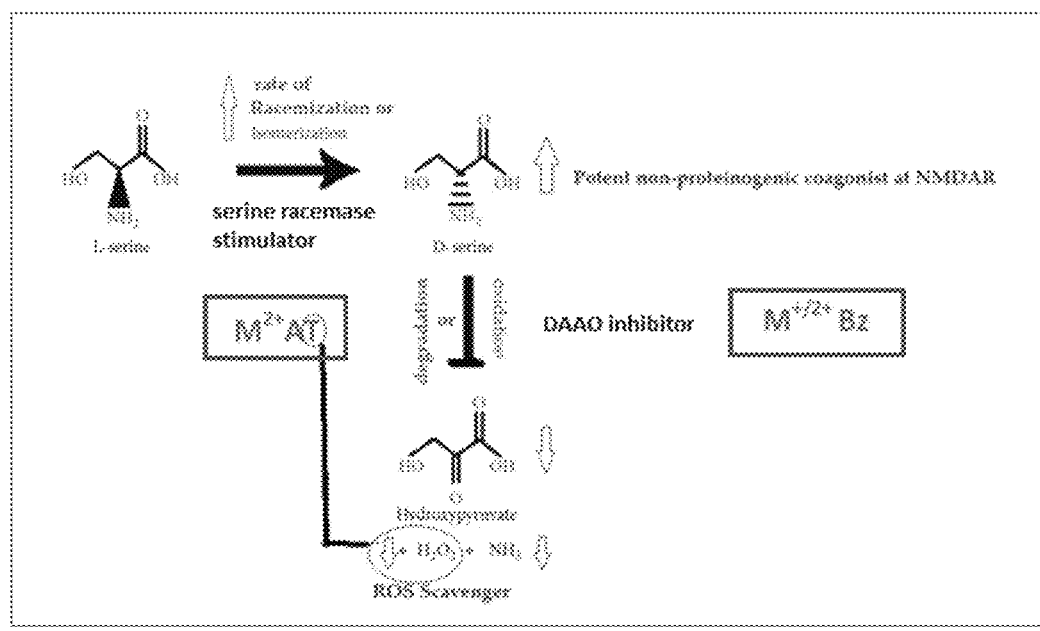
FIG. 1 illustrates schematic presentation of synergistic effect of $M^{2+}AT$ and $M^{+/2+}Bz$ on DSR signaling.

The invention will now be described in detail in connection with certain preferred and optional embodiments, so that various aspects thereof may be more fully interpreted and comprehended. However, any skilled person or artisan will appreciate the extent to which such embodiments could be generalized in practice.

It is further to be understood that all terminology used herein is for the purpose of describing particular embodiments only, and is not intended to be limiting in any manner or scope.

Unless defined otherwise, all technical and scientific expressions used herein have the same meaning as commonly understood by one of ordinary skill in the art to which embodiments of the invention pertain. In describing and claiming the embodiments of the present invention, the following terminology will be used in accordance with the definitions set out below which are known in the state of art.

The singular forms "a", "an", and "the" include plural reference unless the context clearly dictates otherwise. Also the term "composition" does not limit the scope of the invention for multiple compositions that can be illustrated for best mode of the invention.

The term "pharmaceutically/nutraceutically acceptable salt", as use herein, represents those salts which are within the scope of sound medical judgment, suitable for use in contact with the tissues of humans and animals without undue toxicity, irritation, allergic response and the like and are commensurate with a reasonable benefit/risk ratio.

Particularly the term "pharmaceutically-acceptable salts" refers to the relatively non-toxic, inorganic and organic acid addition salts of compounds, mono or divalent metal salts, as well as solvates, co-crystals, polymorphs and the like of the salts.

As used herein, the term "comprising" is intended to mean that the compositions, methods, indications include the recited elements, but not excluding others.

The term "medicinal composition" refers to compositions used to cure a disease or relieve pain. Moreover, the composition comprising active ingredients pertains to curative, healing, officinal, remedial, restorative and therapeutic behavior.

The term "non-proteinogenic" amino acid refers to amino acids which are not coded for by DNA (not present in genetic code). Some amino acids contain the opposite absolute chirality, chemicals that are not available from normal ribosomal translation/transcription machinery.

In current scenario DSR or D-serine is non-proteinogenic which is not naturally encoded by DNA but it is produced endogenously by racemization of naturally coded proteinogenic amino acids called LSR or L-serine.

Moreover DSR is chiral molecule of serine with dextrorotary, which is endogenously synthesized by pyridoxal 5'-phosphate (PLP) binding serine racemase (SR) enzyme catalyzed racemization of levorotatory enantiomer of serine. The SR enzyme is physiologically stimulated or allosterically activated by divalent metal ions (e.g., magnesium) either in free form or in ATP complex.

D-serine amino acid possesses great significance in health, nutrition, and overall metabolism. The term "co-agonist" defines a chemical entity that does not naturally occur in the body and acts on one or more receptors by structural mimicry of the receptors' natural ligand(s).

It may be an agonist or partial agonist for particular receptor, promoting a receptor mediated biological response often by competing with another substance (usually the natural or native substance) at the same receptor at the same receptor.

A partial agonist produces less than the maximum effect even if in a concentration sufficient to bind with all available receptors. D-serine that to co-agonize the NMDA receptor with even greater potency than glycine. It is produced by serine racemase, and is enriched in the same areas as NMDA receptors. It is an optically active amino acid that can combine with a NMDA receptor on a cell to produce a physiologic reaction typical of a naturally occurring substance. Co-agonist implies it is one of other agonists working in conjunction. D-serine can be released both by neurons and astrocytes to regulate NMDA receptors.

NMDA receptors (NMDARs) support patterning and activity of synapses throughout life and are central to many brain disorders. The NMDAR activation requires the concomitant binding of glutamate and a coagonist glycine or D-serine, when NMDAR is activated it allows positively charged ions to flow through the cell membrane. NMDARs also require the binding of the co-agonist glycine for the efficient opening of the ion channel, which is a part of this receptor.

Further the phrase "allosteric regulation" (or allosteric control) defines the regulation of an enzyme by binding an effector molecule at a site other than the enzyme's active site. The site to which the effector binds is termed the allosteric site or regulatory site.

In preferred embodiment, the invention provides novel synergistic medicinal composition for treating or ameliorating dysfunctional D-serine (DSR) signaling.

In particular embodiment, the invention provides potent medicinal composition comprising combination of generally recognized as safe and effective chemical substances or ingredients for enriching endogenous DSR level with no severe side effects.

In preferred embodiment, the invention provides synergistic combination of N-acetyl taurinate salt of divalent metal ($M^{2+}AT$) as serine racemase enzyme (SR) activator/stimulator and benzoic acid ester salt of mono valent or divalent metals ($M^{+/2+}Bz$) as d-amino acid oxidase enzyme (DAAO) inhibitor which are present in specific weight ratio along with pharmaceutically acceptable excipients to enhance the concentration of non-proteinogenic amino acid co-agonist at NMDAR.

In another embodiment, the invention provides synergistic medicinal composition that regulates the concentration of D-serine at NMDAR as non-proteinogenic co-agonist through synergistic effect of two potential therapeutic agents, wherein one agent is N-acetyl taurinate salt of divalent metal and benzoic acid ester salt of mono or divalent metals, wherein the divalent metals are selected from the group consisting of magnesium, manganese, calcium, zinc and the monovalent metals are selected from the group consisting of lithium, potassium and sodium.

In yet another embodiment, the invention provides synergistic medicinal composition wherein one active moiety is N-acetyl taurinate salt of divalent metal, wherein the divalent metal is magnesium. Particularly the one active moiety is magnesium acetyl taurate [MgAT].

According to the invention, DSR is "non-proteinogenic" D-isomer amino acid which is synthesized from naturally encoded "proteinogenic" L-isomer amino acid called LSR. Particularly biosynthesis of DSR from LSR is racemization or isomerization reaction which is catalyzed by pyridoxal-5'-phosphate (PLP) dependent enzyme serine racemase (SR).

The activity of SR enzyme depends on binding motifs that control PLP (pyridoxal phosphate) cofactor binding as well as divalent cations and ATP binding.

Interestingly, the divalent metal ion activates allosterically serine racemase where $Mn^{2+}$ leads to the highest increase in activity of the enzyme (153% @10 µM), followed by Ca' (134% @1 mM) and $Mg^{2+}$ (112% @10 µM) relative to the purified human SR without divalent cation supplementation [Front Mol Biosci. 2019; 6: 8]. However the purpose of taurinate salt in the present composition is not only to improve the bioavailability of divalent metal ion but also to provide antioxidant that reduces hydrogen peroxide ($H_2O_2$)-induced oxidative stress.

The present composition provides highly water soluble and bioaviable salt of divalent cation ($M^{2+}AT$) i.e acetyl taurinate salt of Mn, Mg or Ca wherein the acetyl taurinate salt provides binding site for serine racemase activity thus enhances the rate of racemization of D-serine from L-serine subsequently regulated DSR concentration improve NMDAR activation.

D-serine is a key regulator of NMDAR activity and important physiological ligand at the coagonist site. D-serine synthesis and release, or its metabolism fine tunes NMDAR activation.

Further oxidation of D-serine occurred with the concomitant production of hydrogen peroxide which is regulated by taurinate present in the salt. Taurinate has potential antioxidant effects that subsequently reduce hydrogen peroxide ($H_2O_2$)-induced oxidative stress, neurotoxicity, neuroinflammation.

In another preferred embodiment, the N-acetyl taurinate salt of divalent metal ($M2^+AT$) is magnesium acetyl taurate (MgAT) also known as magnesium acetyl taurinate, ATA-Mg, magnesium acetyl taurinate dehydrate and magnesium 2-acetylamino ethane sulfonic acid.

Figure 4:
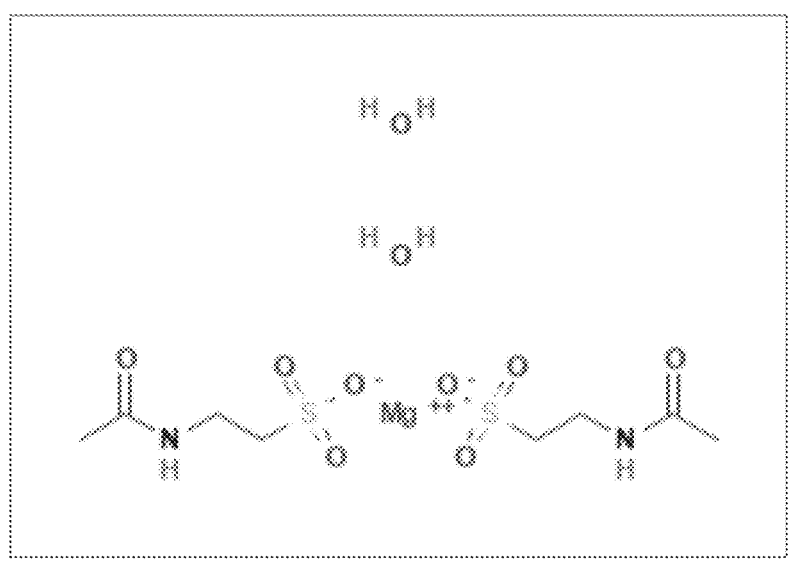
FIG. 4 is a representation of magnesium 2-acetamidoethanesulfonate dihydrate (Formula I) having a chemical formula $C_8H_{20}MgN_2O_{10}S_2$.

MgAT is chemically known as magnesium 2-acetamido-ethanesulfonate dihydrate. It has a chemical formula $C_8H_{20}MgN_2O_{10}S_2$ represented in FIG. 4 as Formula I. Magnesium acetyl taurate is a white powder that is soluble in water.

In another embodiment, the invention provides synergistic medicinal composition comprising a therapeutically effective amount of N-acetyl taurinate salt of divalent metal, wherein $M^{2+}AT$ is present in the range of 1-5000 mg containing 1-500 mg of elemental magnesium ($M^{2+}$) by the weight of total composition.

In another embodiment, the invention provides synergistic medicinal composition comprising therapeutically effective amount of magnesium acetyl taurate present in the range of 1-1000 mg by the weight of total composition.

In another embodiment, the invention provides synergistic medicinal compositions wherein the magnesium acetyl taurate comprises 6 to 8% w/w of elemental magnesium, particularly 6.7% w/w of elemental magnesium by weight of the magnesium acetyl taurate.

Further, the acetyl taurate is present in the range of 91.0%-95.0% w/w, particularly acetyl taurate is present in an amount 94.7% w/w by weight of the magnesium acetyl taurate.

Particularly 250 to 750 mg magnesium acetyl taurate/day providing 17 to 51 mg magnesium/day and 233 to 699 mg acetyl taurate/day, equal to 3.9 to 11.7 mg/kg bw/day for a 60 kg adult.

'Manganese' ($Mn^{2+}$) is an essential trace element; it is needed for good health but is only required in tiny amounts. Further adequate intake of 3 mg/day for all adults while for labeling 2 mg/day is recommended by EFSA.

It is further highlighted that $Mn^{2+}$ is more active at divalent metal binding site of human SR on the other hand $Mg^{2+}$ and $Ca^{2+}$ stimulated/activated SR through divalent metal cation binding as well as ATP binding site. The ATP-$Ca^{2+}$ complex produces a 2-fold lower maximal activation in comparison to the ATP-$Mg^{2+}$ complex and exhibits a 3-fold higher $EC_{50}$ (half maximal effective concentration) [Biochim Biophys Acta Proteins Proteom. 2017 April; 1865 (4): 381-387].

Conversely high doses of D-serine have been reported to cause nephrotoxicity resulting from D-serine oxidation catalyzed by DAAO. D-amino acid oxidase (DAAO) also known as OXDA, DAMOX) is an enzyme with the function on a molecular level to oxidize D-amino acids to the corresponding imino acids, producing β-hydroxypyruvate, ammonia and hydrogen peroxide.

Usually hydrogen peroxide is associated with oxidative stress, whereas large amounts of β-hydroxypyruvate have been shown to induce cell death. Consequently, DAAO inhibition provide protection against potential toxic side effects from high doses of D-serine [Neuropsychopharmacology: 41, 1610-1619(2016)]. Further peripheral DAAO inhibition has the potential of reducing the need for high doses of D-serine.

D-serine undergoes oxidation by D-amino-acid oxidase (DAAO) before it reaches the brain. Consequently, coadministration of D-serine stimulator with a DAAO inhibitor is feasible way to lower the D-serine dose required to treat neurological and psychiatric diseases caused due to dysregulation of D-serine.

In another preferred embodiment, the invention provides synergistic medicinal composition, wherein the other active moiety is $M^{+/2+}Bz$ as d-amino acid oxidase enzyme (DAAO) inhibitor, wherein $M^+$ is monovalent cation or mono valent metal ion and $M^2$ is divalent cation or divalent metal ion and Bz denotes benzoic acid ester or benzoate salt.

In another embodiment the invention provides synergistic medicinal composition, wherein the monovalent metal ions are selected from the group consisting of lithium, potassium, sodium; whereas divalent metal ions are selected from the group consisting of calcium, magnesium, zinc, and manganese.

In certain embodiments the benzoic acid, benzoic acid salt, or derivative thereof is selected from the group consisting of benzoic acid, sodium benzoate, potassium benzoate, calcium benzoate, 2-aminobenzoate, 3-aminobenzoate, and 4-aminobenzoate.

According to the invention, the DAAO inhibitor not only inhibits the degradation or oxidation of D-serine but also reduces neurotoxicity. Therefore, in the present composition the synergistic effect of tuarine and DAAO inhibitors leads to substantial decrease in oxidative stress, excitotoxicity and neuroinflammation.

In another preferred embodiment the benzoic acid ester salt of metal ion is sodium benzoate. Sodium benzoate is an organic sodium salt resulting from the replacement of the proton from the carboxy group of benzoic acid by a sodium ion. Sodium benzoate is a substance which has the chemical formula $C_6H_5COONa$ represented below as Formula II. It is a widely used food preservative, with an E number of E211. It is the sodium salt of benzoic acid and exists in this form when dissolved in water.

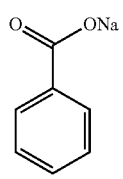

Formula II

In another embodiment, the invention provides synergistic medicinal composition comprising a therapeutically effective amount of benzoate salt of metal ion, wherein $M^{+/2+}Bz$ is present in the range of 1-3000 mg of total composition. Particularly synergistic medicinal composition comprises therapeutically effective amount of sodium benzoate in the range of 1 to 1500 mg of total composition.

In yet another embodiment, the invention provides synergistic medicinal composition comprising combination of $M^{2+}AT$ present in the range of 1-5000 mg containing 1-500 mg of elemental $M^{2+}$ and $M^{+/2+}Bz$ present in the range of 1-3000 mg of total composition.

In yet another embodiment, the invention provides synergistic medicinal composition comprising sodium benzoate present in the range of 1-1000 mg by weight of total composition.

In certain embodiment, the invention provides synergistic medicinal composition comprising therapeutically effective combination magnesium acetyl taurate present in the range of 10 to 750 mg and sodium benzoate present in the range of 10-1000 mg of total composition.

Consequently in the present composition one moiety improves the production of D-serine (DSR) from L-serine (LSR); simultaneously the other moiety inhibits further degradation of D-serine, thus maintaining the optimum D-serine at NMDAR and thereby augment DSR mediated NMDAR function.

In one preferred embodiment the invention provides, a potent synergistic medicinal composition comprising therapeutic combinations of an effective amount of N-acetyl taurinate salt of divalent metal ($M^{2+}AT$) and benzoic acid ester salt of monovalent or divalent metals ($M^{+/2+}Bz$), which are present in the weight ratio of 1:0.001 to 1:1.5 along with pharmaceutically acceptable excipients.

In yet another preferred embodiment, the invention provides novel and stable synergistic medicinal compositions for treating dysfunctional D-serine transmission or signaling comprising synergistic medicinal exogenous blend or combination of N-acetyl taurinate salt of divalent metal ($M^{2+}AT$) and benzoic acid ester salt of monovalent or divalent metals ($M^{+/2+}Bz$) are present in the weight ratio of 1:0.001 to 1:1.5, along with pharmaceutically acceptable excipients.

In certain embodiment, the invention provides the potent synergistic medicinal compositions, wherein divalent metals are selected from the group consisting of magnesium, calcium, manganese, zinc and mono valent metals are selected from the group consisting of lithium, potassium, sodium. In particular embodiment, the divalent metal is magnesium and monovalent metal is sodium present in effective amount.

In one preferred embodiment, the invention provides the potent synergistic medicinal composition, wherein the composition comprises therapeutic combinations of effective amount of magnesium acetyl taurate and sodium benzoate, which are present in the weight ratio of 1:0.001 to 1:1.5 along with pharmaceutically acceptable excipients.

In another preferred embodiment, the invention provides potent synergistic medicinal compositions for treating neuropsychiatric disorders comprising therapeutically effective combination of bioavailable magnesium acetyl taurate and sodium benzoate, which are present in the weight ratio ranging from 1:0.001 to 1:1.5.

In one more embodiment, the invention provides potent and stable synergistic medicinal composition comprising N-acetyl taurinate salt of divalent metal present in a range of 20% to 98% by weight of the total composition.

In another embodiment, the invention provides potent and stable synergistic medicinal composition comprising benzoic acid ester salt of mono or divalent metals which is present in a range of 1% to 50% by weight of the total composition.

In particular embodiment, the invention provides potent and stable synergistic medicinal composition comprising therapeutically effective combination of magnesium acetyl taurate (MgAT) present in a range of 20% to 98% and sodium benzoate present in a range of 1% to 50% by weight of the total composition.

In another preferred embodiment, the invention provides stable, orally active antineuropsychiatric medicinal compositions with enhanced bioavailability comprising synergistic combination of therapeutically effective amount of magnesium acetyl taurate and sodium benzoate which are present in the weight ratio of 1:0.001 to 1:1.5, along with pharmaceutically acceptable excipients.

In another preferred embodiment, the invention provides stable, orally active antineuropsychiatric medicinal composition with enhanced bioavailability, wherein the magnesium acetyl taurate is present in the rage of 20% to 98% and sodium benzoate is present in the range of 1% to 50% by weight of the total composition.

As used herein, the term "therapeutically effective amount" is intended to mean that, 'the amount of active compounds or chemical substances used in the present invention is significantly more effective for regulating D-serine signaling.

Further the regulated D-serine ameliorates NMDAR signaling pathways in brain, pancreas, liver, adipose tissue, and kidney. In another embodiment, the invention provides synergistic medicinal composition, wherein the composition is useful for treating certain neuropsychiatric disorders, neurological disorders and metabolic disorders or specific pathological conditions related to N-methyl-D-aspartate receptors over- or down-regulation.

The term "neuropsychiatric disorder" relates to medical term that encompasses a broad range of medical conditions that involve both neurology and psychiatry. Neuropsychiatry is concerned with disorders of affect, cognition, and behaviour that arise from overt disorder in cerebral function, or from indirect effects of extracerebral disease. It is mental disorders attributable to diseases of the nervous system.

In another embodiment, the invention discloses potent medicinal synergistic composition which is useful for treating neuropsychiatric disorders including but not limited to neurodevelopmental disorders such as attention-deficit/hyperactivity disorder (ADHD), seizures, autism spectrum disorder, and learning disorders, schizophrenia spectrum and other psychotic disorders, bipolar and related disorders, depressive disorders premenstrual dysphoric disorder (pmdd), anxiety disorders, generalized anxiety disorder (gad), cognitive deficit disorders, palsies, uncontrolled anger, migraine headaches. Addictions, hallucination, panic disorder, and phobias (extreme or irrational fears of specific things, such as heights), obsessive-compulsive disorder (OCD), hoarding disorder, and hair-pulling disorder (trichotillomania), trauma and stressor-related disorders, post-traumatic stress disorder (PTSD), acute stress disorder, dissociative identity disorder and dissociative amnesia, illness anxiety disorder, somatic symptom disorder (previously known as hypochondriasis), factitious disorder, feeding and eating disorders, elimination disorders, sleep-wake disorders, sexual dysfunctions, gender dysphoria, disruptive, impulse-control, and conduct disorders, substance-related, addictive disorders, neurocognitive disorders, personality disorders, paraphilic disorders and other mental disorders.

Generally neuropsychiatric disorder include but are not limited to schizophrenia, schizophreniform disorder, brief psychotic disorder, delusional disorder, schizotypal personality disorder, major depressive disorder, bipolar disorder, chronic hallucinatory psychosis, dissociative disorders, obsessive-compulsive disorder, induced delusional disorder, posttraumatic stress disorder, menstrual psychosis, cycloid psychosis depression, mania, bipolar disorder, visual hallucination, auditory hallucination, eating disorder, attention deficit hyperactivity disorder, Tourette's syndrome, other movement disorders, substance dependence (alcohol, cocaine), bipolar affective disorders, or unipolar affective disorder, and adolescent conduct disorder.

Further the term neurological disorders relates to any disorder of the nervous system (central and peripheral nervous system). Structural, biochemical or electrical abnormalities in the brain, spinal cord or other nerves like cranial nerves, peripheral nerves, nerve roots, autonomic nervous system, neuromuscular junction, and muscles can result in a range of symptoms.

These disorders include epilepsy, Alzheimer disease, dementias, cerebrovascular diseases including stroke, migraine and other headache disorders, multiple sclerosis, Parkinson's disease, neuroinfections, brain tumours, traumatic disorders of the nervous system due to head trauma.

Additionally, the term metabolic disorder discloses any disorder occurs when abnormal chemical reactions in human body disrupt the metabolic process. There are different groups of disorders. Some affect the breakdown of amino acids, carbohydrates, or lipids. Another group, mitochondrial diseases, affects the parts of the cells that produce the energy. Metabolic syndrome is a cluster of conditions that occur together, increasing risk of heart disease, stroke, type 2 diabetes, high blood pressure, high blood sugar, overweight, abdominal obesity, excess body fat around the waist, and abnormal cholesterol or triglyceride levels.

In additional embodiment, the invention provides an additional bioenhancer to improve the bioavailability of the present composition by enhancing the absorption of active ingredients inside the body.

In some embodiment, the invention provides synergistic combination of serine ravemase enzyme activator and D-amino-acid oxidase inhibitor present in weight ratio of 1:0.001 to 1:1.5 along with pharmaceutically acceptable excipients augments brain D-serine levels, for the treatment of schizophrenia.

The term "therapeutically effective amount" denotes an amount that reduces the risk, potential, possibility or occurrence of a disease or disorder, or provides advanced alleviation, mitigation, and/or reduction or restoration or modulation, regulation of at least one indicator/biomarker (e.g., blood or serum CRP level), and/or minimize at least one clinical symptom related to dysfunctional DSR signaling.

The term "subject in need thereof" pertains to subject preferably mammal, more preferably human suffering or suspected with neuropsychiatric disorders, neurological and metabolic disorders related to dysregulation of NMDAR and Serine racemase.

The "subject in need thereof" pertains to subject preferably mammal, more preferably human with pre-existing symptoms of neuropsychiatric disorders or in a subject to prevent occurrence of neuropsychiatric disorders or subject with antineuropsychiatric drug intolerance or neuroleptic intolerance or antipsychotic/antineuropsychiatric medication side effects.

In the context of the present invention, the terms "treatment" and the like refer to alleviating, mitigating, prophylaxis, attenuating, managing, regulating, modulating, controlling, minimizing, lessening, decreasing, down regulating, up regulating, moderating, inhibiting, suppressing, limiting, blocking, decreasing, preventing, inhibiting, stabilizing, ameliorating, curing, or healing the neuropsychiatric disorders like schizophrenia.

Notably, the present synergistic composition is water-soluble, non-hazardous, non-toxic and generally recognized as safe for human consumption without any side effects, therefore the present medicinal composition can also be used under preventive therapy/adjuvant therapy/add-on therapy/combination therapy in a subject in need thereof.

In another embodiment, the synergistic composition of the present invention is non-toxic, cost effective, enriched with nutrients or biomolecules and provides safeguard against neural dysfunction from harmful toxins, without any adverse effect.

Certain compounds of the present invention can exist in unsolvated forms as well as solvated forms, including hydrated forms. Certain compounds of the present invention can exist in multiple crystalline or amorphous forms ("polymorphs"). In general, all physical forms are of use in the methods contemplated by the present invention and are intended to be within the scope of the present invention. Compound or a pharmaceutically acceptable salt, hydrate, polymorph or solvate of a compound" intends the inclusive meaning of "or", in that materials meeting more than one of the stated criteria are included, e.g., a material that is both a salt and a solvate is encompassed.

Compounds of the invention can exist in particular geometric or stereoisomeric forms. The invention contemplates all such compounds, including dextrorotatory and levorotatory-isomers. All such isomers, as well as mixtures thereof, are intended to be included in this invention.

As used herein, the term "pharmaceutically acceptable carriers, diluents or excipients" is intended to mean, without limitation, any adjuvant, carrier, excipient, sweetening agent, diluents, preservative, dye/colorant, flavor enhancer, surfactant, wetting agent, dispersing agent, suspending agent, stabilizer, isotonic agent, solvent, emulsifier, or encapsulating agent, encapsulating polymeric delivery systems or polyethyleneglycol matrix, which is acceptable for use in the subject, preferably humans. Excipients may also include, for example: antiadherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration, salts.

In another embodiment, the invention relates to synergistic medicinal composition, which can be prepared in a manner well known in the pharmaceutical art, and can be administered by a variety of routes, depending upon whether local or systemic treatment is desired and upon the area to be treated. The preferable route of administration includes but not limited to sublingual, rectal, topical, parenteral, nasal or oral.

In some embodiment, the present synergistic medicinal composition can be administered to the subject in need thereof, in the form which is suitable for oral use, such as a tablet, capsule (in the form of delayed release, extended release, sustained release, enteric coated release); hard gelatin capsules, soft gelatin capsules in an oily vehicle, veg capsule, hard or soft cellulose capsule, granulate for sublingual use, effervescent or carbon tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, tablets, pellets, granules, capsules, lozenges, aqueous or oily solutions, suspensions, emulsions, sprays or reconstituted dry powdered form with a liquid medium or syrup; for topical use including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by inhalation, such as a finely divided powder or a liquid aerosol; for sub-lingual or buccal use, such as a tablet, capsule, film, spray. Further the composition can be formulated for parenteral use including intravenous, subcutaneous, intramuscular, intravascular, infusion, intraperitoneal, intracerebral, intracerebroventricular, or intradermal.

Formulations of the present invention suitable for oral administration can be presented as discrete units such as capsules (e.g., soft-gel capsules), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion. The active ingredients can also be presented in the form of a a bolus, electuary or paste, nutritional bar, energy bars (candy bars), powder, granule sachet.

Further, the present composition can be formulated in the form of age-appropriate pediatric oral dosage forms such as syrup, minitablets, chewable formulations, orodispersible films orodispersible tablets. It can also be prepared in the form of snack, chocolate bars or other confectionery food products.

Notably, the present synergistic composition is stable, non-hazardous, non-toxic and safe for human consumption without any side effects, therefore the present nutritional composition can also be used under preventive therapy/adjuvant therapy/add-on therapy/combination therapy in a subject in need thereof.

In another embodiment, the synergistic composition of the present invention is non-toxic, cost effective, enriched with nutrients or biomolecules and provides safeguard against problems associated with neurotransmission without any adverse effect.

In another embodiment of the invention, the diluents are selected from starches, hydrolyzed starches, partially pregelatinized starches, anhydrous lactose, cellulose powder, lactose monohydrate, sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulphate, cellulose acetate, corn starch, pregelatinized starch, dextrin, β-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the diluent in the composition/formulation is present in a range of 1% to 30% by weight of the total composition/formulation.

In yet another embodiment of the invention, the binder is selected from disaccharides such as sucrose, lactose, polysaccharides and their derivatives like starches, cellulose, or modified cellulose such as microcrystalline cellulose and cellulose ethers such as hydroxypropyl cellulose (HPC); hydroxypropyl methyl cellulose (HPMC); sugar alcohols such as xylitol, sorbitol, or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, co-povidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose, hydroxyl ethyl methyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methylcellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colorants and wax.

In further embodiment of the invention, the binder in the composition/formulation is present in a range of 0.1 to 40% by weight of the composition/formulation.

In another embodiment of the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulphate, medium-chain triglycerides, mineral oil, myristic acid, palmitic acid, poloxamer, polyethylene glycol, sodium benzoate, sodium chloride, sodium lauryl sulphate, sodium stearyl fumarate, stearic acid, talc, potassium, or sodium benzoate or the like.

In some embodiment of the invention, the lubricant in the composition/formulation is present in a range of 0.1% to 10.0% by weight of the total composition/formulation.

In another embodiment of the invention, the solubilizing agent is selected from polysorbate 80, sodium lauryl sulphate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethyl cellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxpropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like.

In another embodiment of the invention, the amount of solubilizing agent or surfactant in the composition/formulation ranges from 0.1% to 10% by weight of the composition/formulation.

In a preferred embodiment of the invention, the solubilizing agent or surfactant is present in a range of 0.1% to 5.0% by weight of the composition/formulation.

In some embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In another embodiment of the invention, the glidant in the composition/formulation is present in a range of 0.1% to 5.0% by weight of the total composition/formulation.

In some embodiment of the invention, the stabilizers are selected from the group consisting of alginate, agar, carrageen, gelatin, guar gum, gum arabic, locust bean gum, pectin, starch, xanthan gum, trehalose and likewise.

In some embodiment of the invention, the stabilizer in the composition/formulation is present in a range of 0.1% to 8.0% by weight of the total composition/formulation. In some embodiment of the invention, the plasticizers are added to coating formulations selected from the group propylene glycol, glycerol, glyceryl triacetate (triacetin), triethyl citrate, acetyl triethyl citrate, diethyl phthalate, actetylated monoglycerides, castor oil, mineral oil and like thereof.

In some embodiment of the invention, the plasticizer in the composition/formulation is present in a range of 0.1% to 5.0% by weight of the total composition/formulation.

In some embodiment of the invention, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In a preferred embodiment of the invention, the solvent in the composition/formulation is used in a quantity sufficient to make the weight of the composition/formulation 100% by weight.

The additional additives include a polymer, a plasticizer, a sweetener, and a powdered flavor, a preservative, a colorant, a surfactant, and other excipients. The powdered flavor composition includes a flavourant associated with a solid carrier. Coating materials such as synthetic polymers, shellac, corn protein (zein) or other polysaccharides, gelatin, fatty acids, waxes, shellac, plastics, and plant fibers and like thereof are used.

In a preferred embodiment of the invention, the additives are used in a range of 1 to 20% w/w of unit dose.

In yet another embodiment, the invention provides a synergistic nutritional composition comprising a therapeutic blend of a biotin-manganese complex and a stabilized oxaloacetate along with pharmaceutical excipients, wherein the pharmaceutical excipients are selected from a diluent, a binder, a lubricant, a glidant, an additive, a surfactant, a stabilizer or mixtures thereof.

In a preferred embodiment, the diluent is present in a range of 1 to 30%; the binder present is present in a range of 0.1 to 25%; the lubricant is present in a range of 0.1 to 10.0%; the glidant is present in a range of 0.1 to 5.0%; the additive is present in a range of 1 to 10%; the surfactant is present in a range of 0.1 to 5.0%; the stabilizer is present in a range of 0.1 to 5.0%; and the plasticizer is present in a range of 0.1 to 5.0%; by weight of total composition.

In a preferred embodiment, the present medicinal composition/formulation is formulated for oral administration. Specifically, the solid medicinal compositions, are in the form of tablets, capsules, pills, hard capsules filled with liquids or solids, soft capsules, sachets, powders, granules, suspensions, solutions, or modified release formulations. Formulations of the present invention suitable for oral administration are presented as discrete units such as capsules (e.g., soft-gel capsules, hard-gel capsule), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion.

In further embodiment compositions containing compounds of the invention, $M^{2+}AT$ and $M^{+/2+}Bz$, can be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof.

The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 2500 mg per day, preferably about 10 mg per day to about 1000 mg per day. In some embodiments, the total daily dose can range from about 5 mg to about 4000 mg per day, and preferably about 5 mg to about 2000 mg per day.

In another embodiment, the present invention provides a method for treating neuropsychiatric disorders in a subject in need thereof. The method comprises administering an oral dose of a therapeutically effective amount of a medicinal composition comprising an exogenous synergistic combination of magnesium acetyl taurate and sodium benzoate, wherein the magnesium acetyl taurate and sodium benzoate which are present in the a weight ratio of 1:0.001 to 1:1.5, along with pharmaceutically acceptable excipients.

In certain embodiments, the invention provides the potent synergistic medicinal composition wherein the effective unit dose for an oral administration is formulated in a range of 10 to 1000 mg.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art. The present composition can be used as infant formula as well as adult formula by varying the concentration of active ingredients. Further, it is noted that the dietician or nutritionist or certified physician knows how and when to interrupt, adjust or terminate therapy in conjunction with an individual patient's response.

The use of any and all examples, or exemplary language (e.g., such as) provided herein, is intended merely to better illuminate the invention and does not pose a limitation on the scope of the invention unless otherwise claimed.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The invention may be further illustrated by the following examples, which are for illustrative purposes only and should not be construed as limiting the scope of the invention in anyway. The present invention is not to be limited in terms of the particular embodiments described in this application, which are intended as single illustrations of individual aspects of the invention. Functionally equivalent compositions and treatments within the scope of the invention, in addition to those enumerated herein, will be apparent to those skilled in the art from the foregoing description and examples. Such modifications and variations are intended to fall within the scope of the appended claims. The contents of each reference, patent and patent application cited in this application is hereby incorporated by reference in its entirety.

EXAMPLES

Having described the basic aspects of the present invention, the following non-limiting examples illustrate specific embodiments thereof. Those skilled in the art will appreciate that many modifications may be made in the invention without changing the essence of invention.

Example 1 i. Composition 1: Synergistic blend

| Ingredient | w/w % |
| --- | --- |
| Magnesium Acetyl Taurate containing 6.7% w/w elemental Mg | 20 to 98% |
| Sodium Benzoate | 1 to 50% | ii. Composition 2: Tablet/Capsule

| Ingredient | w/w % unit dose |
| --- | --- |
| Magnesium Acetyl Taurate containing 6.7% w/w elemental Mg | 20 to 98% |
| Sodium Benzoate | 1 to 50% |
| Excipient | 5-20% |
| Average Weight | 100% |
| Average weight in mg | 300-500 mg | iii. Composition 3: Tablet/Capsule

| Ingredient | w/w % unit dose |
| --- | --- |
| Magnesium Acetyl Taurate | 20-75% |
| Sodium Benzoate | 1-40% |
| Diluents | 1-10% |
| Binders | 0.5-5% |
| Glidants | 0.5-5% |
| Lubricants | 0.5-5% |
| Stabilizers | 0.1-10% |
| Additives | 1-10% |
| Solvents | QS | iv. Composition 4: Tablet/Capsule

| Ingredient | mg per unit dose |
| --- | --- |
| Magnesium Acetyl Taurate | 50-75 |
| Sodium Benzoate | 1-10 |
| Silicon dioxide | 1-10 |
| Hydroxypropyl Methylcellulose | 1-10 |
| Microcrystalline Cellulose | 1-20 |
| Zinc Stearate | 1-10 |
| PVP K-30 | 5-10 |
| methylated-β-cyclodextrin | 1-10 |
| Polysorbate 80 | 1-10 |
| Manitol | 1-20 |
| Propylene Glycol | QS |
| Water | QS |
| Average weight | 100-150 mg | v. Composition 5: Tablet/Capsule

| Ingredient | mg per unit dose |
| --- | --- |
| Magnesium Acetyl Taurate | 350 |
| Sodium Benzoate | 300 |
| Sodium ascorbate | 1-10 |
| Microcrystalline Cellulose | 2-20 |
| Silicon dioxide | 5-15 |
| Hydroxypropyl Methylcellulose | 2-10 |

-continued

| Ingredient | mg per unit dose |
| --- | --- |
| Magnesium citrate | 2-10 |
| PVP K-30 | 5-10 |
| Talc | 1-10 |
| Tween 80 | 1-10 |
| Manitol | 5-20 |
| Alcohol | QS |
| Water | QS |
| Average weight | 700-800 mg | vi. Composition 6: Tablet/Capsule

| Ingredient | mg per unit dose |
| --- | --- |
| Magnesium Acetyl Taurate | 250 |
| Sodium Benzoate | 100 |
| Sodium ascorbate | 1-10 |
| Microcrystalline Cellulose | 2-20 |
| Silicon dioxide | 5-15 |
| Hydroxypropyl Methylcellulose | 2-10 |
| Magnesium citrate | 2-10 |
| Dibasic calcium phosphate | 1-20 |
| PVP K-30 | 5-10 |
| Talc | 1-10 |
| Tween 80 | 1-10 |
| Manitol | 5-20 |
| Alcohol | QS |
| Water | QS |
| Average weight | 370-450 mg | vii. Composition 7: Tablet/Capsule

| Ingredient | mg per unit dose |
| --- | --- |
| Magnesium Acetyl Taurate | 150 |
| Sodium Benzoate | 50 |
| Microcrystalline Cellulose | 1-10 |
| Silicon dioxide | 1-10 |
| Hydroxypropyl Methylcellulose | 1-10 |
| Magnesium Stearate | 2-10 |
| Polyvinylpyrrolidone | 1-10 |
| Talc | 1-10 |
| Polysorbate 20 | 1-10 |
| Manitol | 1-10 |
| IPA | QS |
| Water | QS |
| Average weight | 200-250 mg | viii. Composition 8: Tablet/Capsule

| Ingredient | mg per unit dose |
| --- | --- |
| Magnesium Acetyl Taurate | 50 |
| Sodium Benzoate | 5 |
| Silicon Dioxide | 1-10 |
| Microcrystalline Cellulose | 2-20 |
| Dibasic Calcium Phosphate | 2-20 |
| Magnesium Stearate | 2-10 |
| Croscarmellose sodium | 2-10 |
| Polyvinylpyrrolidone | 1-20 |
| Talc | 1-10 |
| Sodium ascorbate | 1-10 |
| Propylene glycol | 1-10 |
| Water | QS |
| Average weight | 75-100 mg | ix. Composition 9: Tablet/Capsule/Syrup

| Ingredient | mg per unit dose |
| --- | --- |
| Magnesium Acetyl Taurate | 200 |
| Sodium Benzoate | 5 |
| Microcrystalline Cellulose | 1-10 |
| Silicon dioxide | 1-10 |
| Hydroxypropyl Methylcellulose | 1-10 |
| Magnesium Stearate | 2-10 |
| Polyvinylpyrrolidone | 1-10 |
| 2-Hydroxypropyl-β-cyclodextrin | 1-10 |
| Ascorbic Acid | 1-10 |
| Polysorbate 20 | 1-10 |
| Sucrose | 1-10 |
| Manitol | 1-10 |
| Water | QS |
| Average weight | 225-250 mg |

Example 2: Animal Study

To assess and compare the pharmacokinetics profile of D-serine in rat model.

Test System and Animal Husbandry
  Species: Rats
  Strain: Sprague Dawley
  Sex: Male and Female
  No. of animals: 72 Animals (n=6 per group)
  Age: 8-12 weeks
  Body weight: 230-280 g
Animal House Conditions
  Lighting: 12/12 hour light-dark cycle
  Temperature: 22±3° C.
  Relative Humidity: 30 to 70%
  Animals had continuous access to fresh, potable, uncontaminated drinking water.
  Feed: Normal chow diet
Group, Designation and Dose Levels:
  Six groups were divided into 4 sets of 3 rats each/subset for bleeding and organ (brain) collection—Total 72 rats

TABLE 1

Animal grouping and treatment details

| Groups | Group Description | Animal dose (rat) mg/kg | No. of animals |
| --- | --- | --- | --- |
| Group 1 | Control—Normal | 0.00 | (3 × 4) 12 |
| Group 2 | Disease Control [L-Serine O-sulfate] | 1.86 mg/kg | (3 × 4) 12 |
| Group 3 | Standard [Olanzapine] [10 mg human dose] | 1.03 mg/kg | (3 × 4) 12 |
| Group 4 | Magnesium acetyltaurate-[ 350 mg human dose ] | 36.17 mg/kg | (3 × 4) 12 |
| Group 5 | Sodium benzoate -[300 mg human dose] | 31.01 mg/kg | (3 × 4) 12 |
| Group 6 | Magnesium acetyltaurate + Sodium benzoate- [650 mg human dose] | 67.17 mg/kg | (3 × 4) 12 |

TABLE 2

Sample details
Time points/dose

For Plasma sampling

Set 1 (3 rat) - 0 (Pre-dose)
Set 2 (3 rat) - 2 hr

TABLE 2-continued

Sample details
Time points/dose

Set 3 (3 rat) - 6 hr
Set 4 (3 rat) - 10 hr
For Brain sampling

Set 1 (3 rat) - 0 (Pre-dose)
Set 2 (3 rat) - 2 hr
Set 3 (3 rat) - 6 hr
Set 4 (3 rat) - 10 hr
Total Samples - 72 plasma samples + 72 brain samples.

Blood samples: ~500₄, of blood was collected in tube containing 15% K3-EDTA through retro-orbital bleeding. Plasma was separated using refrigerated centrifuge & stored in −80° C. before analysis. Blood was collected at time point 0, 2, 6 and 10 hrs at least from 3 rats/group/time point.

Organ (Brain) collection: Rats were sacrificed each time point (3 rats/group/time point) by decapitation at 0, 2, 6 or 10 hr post dose. Brain was removed and cerebellum dissected on ice. Tissue samples were frozen on dry ice and stored at −80° C. until analysis.

After concentration step, the extract was commonly resuspended in a solvent with 75% methanol followed by centrifugation at 12,000 rpm for 10 min at 4° C. Supernatant was filtered with 0.2 micron amicon syringe filter (Millipore, Hessen, Germany), then directly transferred into auto sampler vials An Accela™ ultra-high performance liquid chromatography (UHPLC) system (Thermo Fisher, Waltham, USA), coupled online via heated electrospray ionization source (HESI) with a Q-Exactive-Orbitrap mass spectrometer (Thermo Fisher), was employed for global metabolomics profiling with 1 μL sample injection volume. The metabolites were profiled using a C18 Hypersil Gold column (1.9 μm, 2.1×150 mm, Thermo).

The temperature of column oven was set at 35° C. and the sample manager was maintained at 4° C. The eluents acetonitrile and water containing 0.1% formic acid were employed in the electrospray ionization-positive (ESI+) mode.

Mobile Phase for Metabolites—
Phase A solvent: Acetonitrile (ACN)
Phase B solvent: Water containing 0.1% formic acid The flow rate was adjusted at 0.35 mL/min with a linear gradient elution over 20 min. From the start to 3 min, eluent CAN was held at 2%, linearly increased to 25% till 4 min, to 55% during next 4 min, and then to 98% in 15 min. Subsequently, eluent ACN was returned to 50% in 18 min then linearly decreased to 2% (initial conditions) till 20 min.

Fundamental pharmacokinetic parameters such as Area under the plasma concentration-time curve [AUC], Area under the plasma concentration-time curve from time zero to time t [$AUC_t$], Area under the plasma concentration-time curve from time zero to time of last measurable concentration [$AUC_{last}$], Area under the first moment of the plasma concentration-time curve from time zero to infinity [$AUMC_t$], Area under the first moment of the plasma concentration-time curve from time zero to time t [$AUMC_t$], Elimination half-life [t½], Lag time [$T_{lag}$], Time to reach maximum (peak) plasma concentration following drug administration [$T_{max}$], Apparent total body clearance of the drug from plasma [CL], Maximum (peak) plasma drug concentration [Cmax] Apparent total clearance of the drug from plasma after oral administration [CL/F], Last measurable plasma concentration [$C_{last}$], Apparent volume of distribution during terminal phase [Vz], Apparent volume of distribution during terminal phase after non-intravenous administration [Vz/F], Terminal disposition rate constant/ terminal rate constant [λz], Mean residence time [MRT] were obtained from the non-compartmental analysis of the plasma/blood data using WinNonlin. The area under the plasma concentration time curve (AUC) value was calculated to the last quantifiable sample (AUClast) by using the log-linear trapezoidal rule.

Results:

TABLE 3

AUC value at different time interval [Blood Plasma Concentration]

| Plasma Concentration | Time | Conc | ln(C) | AUC | AUMC | R | R_adj |
|---|---|---|---|---|---|---|---|
| Normal control | 0 | 0.15553 | −1.86092 | 0 | 0 | −0.95065 | 0.855609 |
| | 2 | 0.15448 | −1.86769 | 0.31001 | 0.30896 | −0.9104 | 0.65764 |
| | 6 | 0.15431 | −1.86879 | 0.92759 | 2.7786 | | |
| | 10 | 0.15289 | −1.87804 | 1.54199 | 7.68812 | | |
| Diseased Control | 0 | 0.037876 | −3.27344 | 0 | 0 | −0.94043 | 0.826618 |
| | 2 | 0.027781 | −3.5834 | 0.065657 | 0.055562 | −0.97455 | 0.899503 |
| | 6 | 0.025459 | −3.67069 | 0.172137 | 0.472194 | | |
| | 10 | 0.020784 | −3.87357 | 0.264623 | 1.193382 | | |
| Reference standard (Olanzapine) | 0 | 0.907876 | −0.09665 | 0 | 0 | −0.96882 | 0.907929 |
| | 2 | 0.857781 | −0.15341 | 1.765657 | 1.715562 | −0.94192 | 0.77443 |
| | 6 | 0.69459 | −0.36443 | 4.870399 | 13.48177 | | |
| | 10 | 0.660784 | −0.41433 | 7.581147 | 35.03253 | | |
| Test I (MgAT) | 0 | 0.6786 | −0.38772 | 0 | 0 | −0.99917 | 0.997525 |
| | 2 | 0.6074 | −0.49857 | 1.286 | 1.2148 | −0.99983 | 0.999311 |
| | 6 | 0.5124 | −0.66865 | 3.5256 | 9.7932 | | |
| | 10 | 0.4274 | −0.85003 | 3.4052 | 14.490 | | |
| Test II (NaBz) | 0 | 0.6386 | −0.44848 | 0 | 0 | −0.98399 | 0.952348 |
| | 2 | 0.6174 | −0.48224 | 1.256 | 1.2348 | −0.99344 | 0.973834 |
| | 6 | 0.52265 | −0.64884 | 3.5361 | 9.9762 | | |
| | 10 | 0.4072 | −0.89845 | 3.3958 | 16.392 | | |
| Test I + Test II (MgAT + NaBz) | 0 | 0.994232 | −0.00578 | 0 | 0 | −0.9994 | 0.998187 |
| | 2 | 0.91585 | −0.0879 | 1.910082 | 1.8317 | −1 | 0.999992 |
| | 6 | 0.799569 | −0.22368 | 5.34092 | 15.08993 | | |
| | 10 | 0.69872 | −0.35851 | 8.337498 | 38.65916 | | |

TABLE 4

Non-Compartmental Analysis of Plasma Data after Extravascular Input

| Parameter | Unit | Normal Control (Group 1) | Diseased Control (Group 2) | Reference standard (Group 3) | Test I (Group 4) | Test II (Group 5) | Test I + Test II (Group 6) |
|---|---|---|---|---|---|---|---|
| Lambda_z | l/h | 0.001509106 | 0.036271109 | 0.03401739 | 0.0439334 | 0.05202658 | 0.033825313 |
| t1/2 | h | 459.3099544 | 19.11017323 | 20.37625986 | 15.7772256 | 13.3229432 | 20.49196633 |
| Tmax | h | 0 | 0 | 0 | 0 | 0 | 0 |
| Cmax | µg/ml | 0.15553 | 0.037876 | 0.907876 | 0.6786 | 0.6386 | 0.994232 |
| Tlag | h | 0 | 0 | 0 | 0 | 0 | 0 |
| Clast_obs/Cmax | | 0.983025783 | 0.548737987 | 0.727835079 | 0.62982611 | 0.63764485 | 0.702773598 |
| AUC 0-t | µg/ml*h | 1.54199 | 0.264623 | 7.581147 | 3.4052 | 3.3958 | 8.337498 |
| AUC 0-inf_obs | µg/ml*h | 102.8536607 | 0.837641042 | 27.00603521 | 11.1335613 | 10.2225684 | 28.99421726 |
| AUC 0-t/0-inf_obs | | 0.014992077 | 0.315914558 | 0.280720474 | 0.35716643 | 0.40807503 | 0.287557271 |
| AUMC 0-inf_obs | µg/ml*h^2 | 68154.39516 | 22.72175702 | 800.3095839 | 343.207898 | 253.097562 | 855.9145367 |
| MRT 0-inf_obs | h | 662.634608 | 27.12588792 | 29.63447161 | 22.6785944 | 19.1413313 | 29.52018083 |
| Vz/F_obs | (mg)/(µg/ml) | 6.44259E−05 | 61.22011746 | 1.124808214 | 54.3966959 | 45.0630503 | 68.48580764 |
| Cl/F_obs | (mg)/(µg/ml)/h | 9.72255E−08 | 2.220521568 | 0.03826304 | 2.38983186 | 2.34447643 | 2.316553897 |

TABLE 5

AUC value at different time interval [Brain Tissue Sample]

| Plasma Concentration | Time | Conc | ln(C) | AUC | AUMC | R | R_adj |
|---|---|---|---|---|---|---|---|
| Normal control | 0 | 0.096006 | −2.34334 | 0 | 0 | −0.95065 | 0.855609 |
| | 2 | 0.095358 | −2.35012 | 0.191364 | 0.190716 | −0.9104 | 0.65764 |
| | 6 | 0.095253 | −2.35122 | 0.572586 | 1.715185 | | |
| | 10 | 0.094377 | −2.36046 | 0.951846 | 4.745753 | | |
| Diseased Control | 0 | 0.02338 | −3.75586 | 0 | 0 | −0.94043 | 0.826618 |
| | 2 | 0.017149 | −4.06583 | 0.040529 | 0.034298 | −0.97455 | 0.899503 |
| | 6 | 0.015715 | −4.15311 | 0.106257 | 0.291478 | | |
| | 10 | 0.01283 | −4.356 | 0.163348 | 0.736656 | | |
| Reference standard (Olanzapine) | 0 | 0.560417 | −0.57907 | 0 | 0 | −0.96882 | 0.907929 |
| | 2 | 0.529494 | −0.63583 | 1.089912 | 1.058989 | −0.94192 | 0.77443 |
| | 6 | 0.428759 | −0.84686 | 3.006419 | 8.322078 | | |
| | 10 | 0.407891 | −0.89675 | 4.67972 | 21.62502 | | |
| Test I (P19A) | 0 | 0.418889 | −0.87015 | 0 | 0 | −0.99917 | 0.997525 |
| | 2 | 0.374938 | −0.98099 | 0.793827 | 0.749877 | −0.99983 | 0.999311 |
| | 6 | 0.316296 | −1.15108 | 2.176296 | 6.045185 | | |
| | 10 | 0.263827 | −1.33246 | 2.136543 | 9.11728 | | |
| Test II (P19B) | 0 | 0.394198 | −0.9309 | 0 | 0 | −0.98399 | 0.952348 |
| | 2 | 0.381111 | −0.96466 | 0.775309 | 0.762222 | −0.99344 | 0.973834 |
| | 6 | 0.322623 | −1.13127 | 2.182778 | 6.158148 | | |
| | 10 | 0.251358 | −1.38088 | 2.230741 | 10.05679 | | |
| Test I + Test II (P19A + P19B) | 0 | 0.613723 | −0.48821 | 0 | 0 | −0.9994 | 0.998187 |
| | 2 | 0.56534 | −0.57033 | 1.179063 | 1.130679 | −1 | 0.999992 |
| | 6 | 0.493561 | −0.70611 | 3.296864 | 9.31477 | | |
| | 10 | 0.431309 | −0.84093 | 5.146604 | 23.86368 | | |

TABLE 6

Non-Compartmental Analysis of Brain Tissue Sample after Extravascular Input

| Parameter | Unit | Normal Control (Group 1) | Diseased Control (Group 2) | Reference standard (Group 3) | Test I (Group 4) | Test II (Group 5) | Test I + Test II (Group 6) |
|---|---|---|---|---|---|---|---|
| Lambda_z | l/h | 0.001509106 | 0.036271109 | 0.03401739 | 0.043933401 | 0.052026581 | 0.033825313 |
| t1/2 | h | 459.3099544 | 19.11017323 | 20.37625986 | 15.77722556 | 13.32294318 | 20.49196633 |
| Tmax | h | 0 | 0 | 0 | 0 | 0 | 0 |
| Cmax | µg/ml | 0.096006173 | 0.023380247 | 0.560417284 | 0.418888889 | 0.394197531 | 0.613723457 |
| Tlag | h | 0 | 0 | 0 | 0 | 0 | 0 |
| Clast_obs/Cmax | | 0.983025783 | 0.548737987 | 0.727835079 | 0.629826113 | 0.637644848 | 0.702773598 |
| AUC 0-t | µg/ml*h | 0.951845679 | 0.163347531 | 4.67972037 | 2.13654321 | 2.230740741 | 5.146603704 |
| AUC 0-inf_obs | µg/ml*h | 63.48991403 | 0.517062372 | 16.67039211 | 7.341704504 | 6.162079271 | 17.89766498 |
| AUC 0-t/0-inf_obs | | 0.014992077 | 0.315914558 | 0.280720474 | 0.357166426 | 0.40807503 | 0.287557271 |
| AUMC 0-inf_obs | µg/ml*h^2 | 42070.6143 | 14.02577594 | 494.0182617 | 211.8567273 | 156.233063 | 528.3423066 |

TABLE 6-continued

Non-Compartmental Analysis of Brain Tissue Sample after Extravascular Input

| Parameter | Unit | Normal Control (Group 1) | Diseased Control (Group 2) | Reference standard (Group 3) | Test I (Group 4) | Test II (Group 5) | Test I + Test II (Group 6) |
|---|---|---|---|---|---|---|---|
| MRT 0-inf_obs | h | 662.634608 | 27.12588792 | 29.63447161 | 22.67859438 | 19.14133125 | 29.52018083 |
| Vz/F_obs | (mg)/(μg/ml) | 0.104369994 | 99.17659028 | 1.822189306 | 88.12248404 | 73.00214148 | 110.9470084 |
| Cl/F_obs | (mg)/(μg/ml)/h | 0.000157505 | 3.597244939 | 0.061986124 | 3.871520447 | 3.798051816 | 3.752817314 |

Discussion

D-serine concentration-time profiles in plasma after oral administration of D-serine were shown in FIGS. 2 and 3, and the pharmacokinetic parameters were summarized in Table 4 and 6. D-Serine was substantially reduced when treated with serine racemase inhibitor i.e., L-Serine 0-sulfate over control. When composition G6 was given the $C_{max}$ and AUC were increased as compared to individual test samples G4 and G5.

AUC values of D-serine were increased in a G4 and G5 dose-dependent manner in plasma and brain tissue samples. The increase in the AUC values of test sample with serine racemaze enzyme activator i.e Group 4 and test sample with DAAO inhibitor i.e., Group 5 were observed at dose 36.17 mg/kg and 31.01 mg/kg respectively.

When G6 was administered with dose 67.17 mg/kg, it has shown significant increase in the AUC of plasma D-serine in MgAT+NaBz dose-dependent manner. The combination product further showed improved or enhanced D-serine level as compared to reference or marketed sample olazapine at dose 1.03 mg/kg.

The oral administration of effective dose of present composition increases the plasma D-serine level by 5 to 8 folds over control.

The oral administration of effective dose of present composition increase the plasma D-serine level by more than 55% as compared to individual active ingredient.

According to the pharmacokinetics profile serine racimase (SR) enzyme activator and DAAO inhibitor are concurrently effective in enhancing plasma d-serine levels in a subject. In a concluding manner AUC of plasma concentration of combination of test samples in appropriate ratio gives synergistic effect with significant increase in plasma D-serine level.

The invention claimed is:

1. A synergistic medicinal composition, comprising: therapeutically active, medicinal ingredients and pharmaceutically acceptable excipients, wherein the therapeutically active, medicinal ingredients consisting of magnesium acetyl taurate and sodium benzoate in a weight ratio of 1:0.001 to 1:1.5, wherein the composition is effective for treating dysfunctional D-serine signaling.

2. The potent synergistic medicinal composition according to claim 1, wherein the magnesium acetyl taurate is present in a range of 20% to 98% by weight of the total composition.

3. The potent synergistic medicinal composition according to claim 1, wherein the sodium benzoate is present in a range of 1% to 50% by weight of the total composition.

4. The potent synergistic medicinal composition according to claim 1, wherein the pharmaceutically acceptable excipients are selected from the group consisting of a diluent present in a range of 1 to 30%; a binder present in a range of 0.1 to 25%; a lubricant present in a range of 0.1 to 5.0%; a glidant present in a range of 0.1 to 5.0%; an additive present in a range of 1 to 10%; a surfactant present in a range of 0.1 to 5.0%; a stabilizer present in a range of 0.1 to 5.0%; and a plasticizer present in a range of 0.1 to 5.0%, by weight of the total composition.

5. The potent synergistic medicinal composition according to claim 1, wherein an effective unit dose of the composition for an oral administration is formulated in a range of 10 mg to 1000 mg.

* * * * *